United States Patent
Peng et al.

(10) Patent No.: US 11,994,503 B2
(45) Date of Patent: May 28, 2024

(54) COMPUTER SYSTEMS AND METHODS FOR ESTIMATING CHANGES IN FUGITIVE EMISSIONS

(71) Applicant: Molex, LLC, Lisle, IL (US)

(72) Inventors: Wenfeng Peng, North Aurora, IL (US); Ling-Ying Lin, Bloomingdale, IL (US); Alissa Nedossekina, West Lafayette, IN (US)

(73) Assignee: Molex, LLC, Lisle, IL (US)

( * ) Notice: Subject to any disclaimer, the term of this patent is extended or adjusted under 35 U.S.C. 154(b) by 0 days.

(21) Appl. No.: 17/778,743

(22) PCT Filed: Nov. 20, 2020

(86) PCT No.: PCT/US2020/061407
§ 371 (c)(1),
(2) Date: May 20, 2022

(87) PCT Pub. No.: WO2021/102211
PCT Pub. Date: May 27, 2021

(65) Prior Publication Data
US 2023/0003705 A1    Jan. 5, 2023

Related U.S. Application Data

(60) Provisional application No. 62/938,972, filed on Nov. 22, 2019.

(51) Int. Cl.
*G01N 33/00*    (2006.01)
*G01M 3/04*    (2006.01)
(Continued)

(52) U.S. Cl.
CPC .......... *G01N 33/0075* (2013.01); *G01M 3/04* (2013.01); *G06Q 30/018* (2013.01)

(58) Field of Classification Search
CPC .... G01N 33/0075; G01M 3/04; G06Q 30/018
See application file for complete search history.

(56) References Cited

U.S. PATENT DOCUMENTS 5,206,818 A * 4/1993 Speranza ............. G01N 1/2273
73/40.5 R
6,058,102 A    5/2000 Drysdale et al.
(Continued)

FOREIGN PATENT DOCUMENTS

| EP | 1881386 A1 | 1/2008 |
|----|------------|--------|
| WO | 2011060418 A2 | 5/2011 |
| WO | 2019068178 A1 | 4/2019 |

OTHER PUBLICATIONS

Epperson et al., "Equivalent Leak Definitions for Smart LDAR (LeakDetection and Repair) When Using Optical Imaging Technology", Journal of the Air & Waste Management Association, Retrieved from Internet URL: https://www.tandfonline.com/doi/pdf/10.3155/1047-3289.57.9.1050, vol. 57, pp. 1050-1060, Sep. 2007.

(Continued)

*Primary Examiner* — Mohamed Charioui
*Assistant Examiner* — Lynda Dinh

(57) ABSTRACT

Computer systems, methods, and apparatuses for estimating changes in gas emissions are described. A computer system may monitor overall emission levels based on sensor outputs from a plurality of gas sensors in a facility. The computer system may estimate a total emission level over a time interval based on the accumulative, gas-response-factor weighted detections of the gas sensors. Emissions from maintenance activities may be excluded as appropriate. The total emission level may be compared with total emission level estimated from different time intervals and/or different facilities. The computer system may be further used for (Continued)

comparing emissions across multiple facilities, or emissions from facilities across multiple regions.

10 Claims, 13 Drawing Sheets

(51) Int. Cl.
    *G06Q 30/01*     (2023.01)
    *G06Q 30/018*     (2023.01)

(56) References Cited

U.S. PATENT DOCUMENTS

| | | | |
|---|---|---|---|
| 9,862,144 B2* | 1/2018 | Lane | B29C 70/44 |
| 10,203,311 B2* | 2/2019 | Risk | G01P 13/02 |
| 2012/0016597 A1 | 1/2012 | Sutan | |
| 2018/0128794 A1 | 5/2018 | Sutan | |
| 2018/0330594 A1 | 11/2018 | Hummer et al. | |
| 2021/0232741 A1* | 7/2021 | Ogiso | G01M 3/38 |

OTHER PUBLICATIONS

International Search Report and Written Opinion received for PCT Application No. PCT/US2020/061407, dated Mar. 5, 2021, 11 Pages.

T. C. O'Haver, "A Pragmatic Introduction to Signal Processing with applications in Chemical Analysis", Department of Chemistry and Biochemistry University of Maryland, Retrieved from Internet URL:http://citeseerx.ist.psu.edu/viewdoc/download?doi=10.1.1.608.8863&rep=rep1&type=pdf, 121 Pages, 1997.

"Protocol for Equipment Leak Emissions Estimates", United States Environmental Protection Agency, Retrieved from Internet URL: https://www3.epa.gov/ttnchie1/efdocs/equiplks.pdf, 403 Pages, Nov. 1995.

* cited by examiner

300

| Chemical Name | Formula | Ionization Potential, eV | Response Factors |
|---|---|---|---|
| Acetone | $C_3H_6O$ | 9.71 | 0.9 |
| Benzene | $C_6H_6$ | 9.25 | 0.53 |
| Butadiene | $C_4H_6$ | 9.07 | 0.85 |
| Butane | $C_4H_{10}$ | 10.53 | 67 |
| Cyclohexane | $C_6H_{12}$ | 9.86 | 1.4 |
| Cyclohexene | $C_6H_{10}$ | 8.95 | 0.8 |
| Dimethylamine | $C_2H_7N$ | 8.23 | 1.5 |
| Ethylene | $C_2H_4$ | 10.51 | 9 |
| Formaldehyde | $CH_2O$ | 10.87 | No response |
| Hexane, n- | $C_6H_{14}$ | 10.13 | 4.3 |
| Iso-butylene | $C_4H_8$ | 9.24 | 1 |
| Isopropanol | $C_3H_8O$ | 10.12 | 6 |
| Mesitylene | $C_9H_{12}$ | 8.41 | 0.35 |
| Methyl mercaptan | $CH_4S$ | 9.44 | 0.54 |
| Naphthalene | $C_{10}H_8$ | 8.13 | 0.42 |
| Octane, n- | $C_8H_{18}$ | 9.82 | 1.8 |
| Pentane | $C_5H_{12}$ | 10.22 | 8.4 |
| Propylene | $C_3H_6$ | 9.73 | 1.4 |
| Styrene | $C_8H_8$ | 8.43 | 0.4 |
| Toluene | $C_7H_8$ | 8.82 | 0.5 |
| Triethylamine | $C_6H_{15}N$ | 7.3 | 0.9 |
| Vinyl chloride | $C_2H_3Cl$ | 9.99 | 2 |

FIG. 3

Pine Oak Plant Maintenance Dashboard

Latest Maintenance Activity 20 results

| | REPORT ID | UNIT | LEVEL | AREA | EXPECTED START DATE | EXPECTED END DATE |
|---|---|---|---|---|---|---|
| ☐ | 20-PW-00215 | Unit A | 1 | ⊙ | 09/25/2020 12:00 AM | 09/26/2020 12:00 AM |
| ☐ | 20-PW-00214 | Unit A | 1 | ⊙ | 11/01/2020 12:00 AM | 12/31/2020 12:00 AM |
| ☐ | 20-PW-00213 | Unit B | 4 | ⊙ | 09/24/2020 12:00 AM | 09/30/2020 12:00 AM |
| ☐ | 20-PW-00212 | Unit A | 1 | ⊙ | 09/01/2020 12:00 AM | 09/02/2020 12:00 AM |
| ☐ | 20-PW-00211 | Unit D | 1 | ⊙ | 08/28/2020 12:00 AM | 08/30/2020 12:00 AM |
| ☐ | 20-PW-00210 | Unit B | 1 | ⊙ | 08/16/2020 12:00 AM | 08/26/2020 12:00 AM |
| ☐ | 20-PW-00209 | Unit B | 1 | ⊙ | 08/01/2020 12:00 AM | 08/30/2020 12:00 AM |
| ☐ | 20-PW-00208 | Unit F | 2 | ⊙ | 08/01/2020 12:00 AM | 08/15/2020 12:00 AM |
| ☐ | 20-PW-00207 | Unit A | 1 | ⊙ | 08/01/2020 12:00 AM | 08/12/2020 12:00 AM |
| ☐ | 20-PW-00206 | Unit C | 1 | ⊙ | 07/10/2020 12:00 AM | 07/15/2020 12:00 AM |
| ☐ | 20-PW-00205 | Unit D | 1 | ⊙ | 07/10/2020 12:00 AM | 07/11/2020 12:00 AM |
| ☐ | 20-PW-00204 | Unit A | 1 | ⊙ | 07/01/2020 12:00 AM | 07/08/2020 12:00 AM |

FIG. 9

|  | Ongoing<br>1 | Planned<br>2 | Completed<br>17 |
|---|---|---|---|
| WORK DESCRIPTION | STATUS ↓ | SENSORS AFFECTED | |
| Pump tune-up | Planned | S-17, S-20, S-30 | |
| Replaced valve | Planned | S-21 | |
| Replaced valve | Ongoing | S-50 | |
| Upgrade pressure transmitter | Completed | S-05, S-06 | |
| Storage vessel clean-up | Completed | S-115 | |
| Pump tune-up | Completed | S-52, S-53 | |
| Regular service of liquid distribution system | Completed | S-77 | |
| Storage vessel clean-up | Completed | S-207 | |
| Pump tune-up | Completed | S-08, S-09, S-12 | |
| Replaced valve | Completed | S-97, S-99 | |
| Replaced valve | Completed | S-115 | |
| Dismantle unused piping system | Completed | S-21, S-22, S-25, S-30 | |

908 — Filter
910 — Text search
912

FIG. 9 (Continued)

COMPUTER SYSTEMS AND METHODS FOR ESTIMATING CHANGES IN FUGITIVE EMISSIONS

CROSS-REFERENCE TO RELATED APPLICATIONS

This application is a national phase of PCT/US2020/061407, filed on Nov. 20, 2020, which claims the benefit of priority to U.S. Provisional Application No. 62/938,972, filed on Nov. 22, 2019. The above-referenced applications are hereby incorporated by reference in their entireties.

TECHNICAL FIELD

Aspects described herein generally relate to gas detection systems and more specifically to monitoring fugitive gas emissions. Aspects of the disclosure relate to a smart digital platform that collects, analyzes, and renders appropriate information about fugitive gas emissions identified by a sensor network-based emissions monitoring system in a facility.

DESCRIPTION OF RELATED ART

The concern for clean living, working, and the industrial environment has increased over the recent decades. The United States Environmental Protection Agency (EPA) promulgated, as part of leak detection and repair (LDAR) programs, Method 21 to determine and limit fugitive emissions of gases from industrial facilities (e.g., petroleum refineries, chemical manufacturing facilities, etc.). Fugitive gases may include, but are not limited to, volatile organic compounds (VOCs) and volatile hazardous air pollutants (VHAPs). Such LDAR programs are widely adopted in the United States.

The EPA has specified techniques for measuring/estimating/monitoring fugitive emissions in a November 1995 document entitled "Protocol for Equipment Leak Emissions Estimates". In general, an industrial facility has to conduct manual Method 21-specified inspections at individual components of the facility using a portable gas monitoring equipment (e.g., VOC analyzers) and record the highest measured value for each component. The EPA-specified correlation factors are then applied to the measured values in order to approximate the total emissions for the facility.

In execution of EPA Method 21, an inspector places an extractive hand-held probe in direct contact with the component under test and traces its circumference, waiting an appropriate amount of time to register a reading of leak concentration (mixing ratio of combustible fraction). If the highest concentration reading is above a control limit, typically 500 to 2000 parts per million, then the component is tagged for repair. The EPA Method 21-determined concentrations are sometimes used to approximate mass flow rates through correlation equations to estimate annual emission leak rates for the facility—a procedure with several sources of uncertainty. It is well known that manual leak detection methods to monitor and repair sources of fugitive emissions are resource intensive and difficult to apply on hard-to-reach sources. Additionally, EPA Method 21 is expensive to execute and can produce safety concerns for inspectors. This manual inspection procedure only checks a subset of potential emissions points inside a facility and possesses high temporal latency since some components may not be visited for more than a year, creating the potential for a leak to go undetected for an extended time.

Many LDAR programs rely heavily on the EPA's Method 21. As described above, Method 21, however, has a number of drawbacks including: (a) heavy reliance on manual inspections with a portable instrument; (b) extreme inefficiencies (e.g., only a small percentage of all components inspected may have active leaks); (c) safety issues related to manual measurements (e.g., technicians may have to climb towers, may be exposed to inhospitable conditions such as high temperatures, and/or may need to access difficult to reach components); (d) high labor costs; and (e) long time periods between LDAR cycles (e.g., during which large leaks and emissions may remain undetected). For example, due to the infrequent monitoring schedule, some large leaks may not be detected in a timely manner and, therefore, the total emissions estimations may not be accurate.

SUMMARY

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure. It is noted that various connections between elements are discussed in the following description. It is noted that these connections are general and, unless specified otherwise, may be direct or indirect, wired or wireless, and that the specification is not intended to be limiting in this respect.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a system for estimating change in overall fugitive emission levels at an industrial facility equipped with a plurality of sensors. The system also includes an emissions monitoring platform that may include at least one first processor and a first memory storing first computer-readable instructions that, when executed by the at least one first processor, cause the emissions monitoring platform to: select, based on a gas stream measured by the plurality of sensors, a response factor for the plurality of sensors using an algorithm disclosed herein; receive, from the plurality of sensors, sensor outputs associated with gas plume detections in a time interval; determine an emission indicator value based on detection events in a sensor output associated with a sensor of the plurality of sensors, where the determining excludes those detection events corresponding to a maintenance activity; determine, based on corresponding emission indicator values and corresponding response factors for the plurality of sensors, a total emission indicator value for the industrial facility in the time interval; determine a difference between the total emission indicator value for the industrial facility in the time interval and a second total emission indicator value for the facility in a second time interval; and send an indication of the difference. The system also includes a user computing device configured to display, on a display device coupled to the user computing device, the indication of the difference. Other embodiments of this aspect include corresponding computer systems, apparatus, and computer programs recorded on one or more computer storage devices, each configured to perform the actions of the methods.

Implementations may include one or more of the following features. The system where the first memory stores first computer-readable instructions that, when executed by the at least one first processor, cause the emissions monitoring platform to determine, for the sensor in the plurality of sensors, the detection events based on the sensor output and modeled baseline values corresponding to the sensor output. The first memory stores first computer-readable instructions that, when executed by the at least one first processor, cause the emissions monitoring platform to determine a detection event, among the detection events, at a first time (T1) based on a difference between the modeled baseline value at the first time and a value of a sensor detection peak at the first time based on the sensor output exceeding a threshold. The first memory stores first computer-readable instructions that, when executed by the at least one first processor, cause the emissions monitoring platform to determine, for each sensor, a signal-to-noise ratio, where the threshold is a multiple of the signal-to-noise ratio. The first memory stores first computer-readable instructions that, when executed by the at least one first processor, cause the emissions monitoring platform to determine the emission indicator value for the sensor based on aggregating peak areas associated with the detection events in the sensor output. The first memory stores first computer-readable instructions that, when executed by the at least one first processor, cause the emissions monitoring platform to determine the emission indicator value for the sensor based on aggregating peak heights associated with the detection events in the sensor output. The location tracking device is configured to: transmit, to the emissions monitoring platform, an indication of a location of the location tracking device and a time stamp associated with the location; where the first memory stores first computer-readable instructions that, when executed by the at least one first processor, cause the emissions monitoring platform to: determine, based on the location, the sensor; determine, based on the time stamp, the one or more detection events in the sensor output. The first computer-readable instructions, when executed by the at least one first processor, cause the emissions monitoring platform to: receive, from the user computing device, indications of a maintenance time interval and a location associated with the maintenance activity; determine, based on the location, the sensor; determine, based on the time interval, the one or more detection events in the sensor output. The first computer-readable instructions, when executed by the at least one first processor, cause the emissions monitoring platform to: determine a third total emission indicator value for a second facility in the time interval; determine a second difference between the total emission indicator value and the third total emission indicator value; and send, to the user computing device, an indication of the second difference; and where the user computing device is configured to display, on the display device, one or more of the total emission indicator value, the third total emission indicator value, and the second difference. The plurality of sensors may include at least one sensor selected from: electrochemical sensors; infrared sensors; catalytic bead sensors; metal oxide semiconductor sensors; photoionization detectors; flame ionization detectors; thermal conductivity sensors; colorimetric sensors; and combination thereof. The determining the total emission indicator value for the industrial facility may include determining a sum of products of corresponding emission indicator values and corresponding response factors for the plurality of sensors. Implementations of the described techniques may include hardware, a method or process, or computer software on a computer-accessible medium.

One general aspect includes a method for estimating change in overall fugitive emission levels at an industrial facility. The method also includes receiving, at an emissions monitoring platform and from a plurality of sensors, sensor outputs associated with gas plume detections in a time interval. The method also includes for a sensor in the plurality of sensors: determining, based on detection events in a sensor output associated with the sensor, one or more emission values; and determining, a response factor for a gas stream based on the composition of the gas stream and response factors of species of any gases in the gas stream. The method also includes determining, based on the one or more emission values and corresponding response factors for the sensors, a total emission value for the facility in the time interval. The method also includes determining a difference between the total emission value for the facility in the time interval and a second total emission value for the facility in a second time interval. The method also includes sending, to a user computing device, an indication of the difference. Other embodiments of this aspect include corresponding computer systems, apparatus, and computer programs recorded on one or more computer storage devices, each configured to perform the actions of the methods.

One general aspect includes a non-transitory computer readable medium storing instructions that include receiving, from a plurality of sensors in a facility, sensor outputs associated with gas concentration measurements in a time interval. The instructions also include for a sensor in the plurality of sensors: determining, based on detection events in a sensor output associated with the sensor, an emission value, where the detection events exclude one or more detection events, corresponding to a maintenance activity, in the sensor output; and determining, a response factor for a gas stream based on the composition of the gas stream and response factors of species of any gases in the gas stream. The instructions also include determining, based on corresponding emission values and corresponding response factors for the sensors, a total emission value for the facility in the time interval. Other embodiments of this aspect include corresponding computer systems, apparatus, and computer programs recorded on one or more computer storage devices, each configured to perform the actions of the methods.

Implementations may include one or more of the following features. The non-transitory computer readable medium further storing instructions that, when executed, cause: determining a difference between the total emission value for the facility in the time interval and a second total emission value for the facility in a second time interval; and/or sending, to a user computing device, an indication of the difference. Implementations of the described techniques may include hardware, a method or process, or computer software on a computer-accessible medium.

One general aspect includes an emissions monitoring platform configured to estimate change in overall fugitive emission levels at an industrial facility. The emissions monitoring platform may include at least one first processor and a first memory storing first computer-readable instructions that, when executed by the at least one first processor, cause the emissions monitoring platform to: select, based on at least one gas species in a gas stream measured by a plurality of sensors at the industrial facility, a response factor for the gas stream; receive, from the plurality of sensors, sensor outputs associated with gas plume detections in a time interval; determine an emission indicator value based on detection events in a sensor output associated with a sensor of the plurality of sensors; determine, based on corresponding emission indicator values and corresponding response factors for the plurality of sensors, a total emission indicator value for the industrial facility in the time interval; and send the total emission indicator value. The system also includes a user computing device configured to output, on a display device coupled to the user computing device, the total emission indicator value. Other embodiments of this aspect include corresponding computer systems, apparatus, and computer programs recorded on one or more computer storage devices, each configured to perform the actions of the methods.

One general aspect includes a method comprising: receiving, at an emissions monitoring platform and from a plurality of sensors, sensor outputs associated with gas plume detections in a time interval at an industrial facility. The method also includes for a sensor in the plurality of sensors: determining, based on detection events in a sensor output associated with the sensor, one or more emission indicator values; and determining, a response factor for a gas stream based on the composition of the gas stream and response factors of species of any gases in the gas stream. The method also includes determining that maintenance activity occurred at the industrial facility during the time interval. The method also includes excluding from the one or more emission indicator values, those detection events corresponding to the maintenance activity. The method also includes determining after the excluding step, based on the one or more emission indicator values and corresponding response factors for the sensors, a total emission indicator value for the industrial facility in the time interval. The method also includes determining a difference between the total emission indicator value for the industrial facility in the time interval and a second total emission indicator value for the industrial facility in a second time interval. Other embodiments of this aspect include corresponding computer systems, apparatus, and computer programs recorded on one or more computer storage devices, each configured to perform the actions of the methods. Implementations may include one or more of sending, to a user computing device, an indication of the difference. Implementations of the described techniques may include hardware, a method or process, or computer software on a computer-accessible medium.

One general aspect includes a method for comparing overall fugitive emission levels at a first facility and at a second facility. The method also includes for the first facility: selecting, based on at least one gas species in a gas stream measured by a plurality of sensors at the first facility, a response factor for the gas stream; receiving, from the plurality of sensors, sensor outputs associated with gas plume detections in a time interval; determining an emission indicator value based on detection events in a sensor output associated with a sensor of the plurality of sensors; and determining, based on corresponding emission indicator values and corresponding response factors for the plurality of sensors, a total emission indicator value for the first facility in the time interval. The method also includes for the second facility: selecting, based on at least one gas species in a gas stream measured by a plurality of sensors at the second facility, a response factor for the gas stream; receiving, from the plurality of sensors, sensor outputs associated with gas plume detections in a time interval; determining an emission indicator value based on detection events in a sensor output associated with a sensor of the plurality of sensors; and determining, based on corresponding emission indicator values and corresponding response factors for the plurality of sensors, a total emission indicator value for the second facility in the time interval. The method also includes determining a difference between the total emission value of the first facility in the time interval and the total emission value of the second facility in the time interval. The method also includes sending, to a user computing device with a display device, an indication of the difference for display. Other embodiments of this aspect include corresponding computer systems, apparatus, and computer programs recorded on one or more computer storage devices, each configured to perform the actions of the methods.

Methods, apparatuses, and systems for monitoring gas emissions in a facility are described. An emissions monitoring sensor network system may monitor overall emission levels based on sensor outputs from a plurality of gas sensors in a facility. The emissions monitoring system may estimate a total emission level over a time interval based on the accumulative, gas-response-factor weighted detections of the gas sensors. Emissions from maintenance activities may be excluded as appropriate. The total emission level may be compared with total emission level estimated from different time intervals and/or different facilities. The emissions monitoring system may be further used for comparing emissions across multiple facilities, or emissions from facilities across multiple regions.

For example, the entirety of features disclosure herein contemplates a system for comparing fugitive emission rates at a first unit and at a second unit at one or more industrial facilities, with each of the one or more facilities being equipped with a plurality of sensors. The system may comprise one or more emissions monitoring platforms and one or more user computing devices. In one embodiment, an emissions monitoring platform comprises at least one first processor and a first memory storing first computer-readable instructions that, when executed by the at least one first processor, cause the emissions monitoring platform to perform a method comprising to: (i) select, based on at least one gas species in a gas stream measured by the plurality of sensors, a response factor for the gas stream; (ii) receive, from the plurality of sensors, sensor outputs associated with gas plume detections in a time interval; (iii) determine an emission indicator value based on detection events in a sensor output associated with a sensor of the plurality of sensors, wherein the determining excludes those detection events corresponding to a maintenance activity; (iv) determine, based on corresponding emission indicator values and corresponding response factors for the plurality of sensors, a total emission indicator value for the industrial facility in the time interval; (v) determine a difference between the total emission indicator value for the industrial facility in the time interval and a second total emission indicator value for the facility in a second time interval; and/or (vi) send an indication of the difference. One or more of steps (i)-(vi) may be optional and/or performed in an order different than enumerated, as appropriate. The one or more user computing devices may be configured to display, on a display device coupled to a user computing device, the indication of the difference sent in step (vi).

In another example involving the aforementioned system for comparing fugitive emission rates at a first unit and at a second unit at one or more industrial facilities, the system may also comprise one or more emissions monitoring platforms and, optionally, one or more user computing devices. The one or more emissions monitoring platforms may perform a method for the first unit comprising one or more steps of: (i) selecting, based on at least one gas species in a gas stream measured by a plurality of sensors at the first unit, a response factor for the gas stream; (ii) receiving, from the plurality of sensors at the first unit, sensor outputs associated with gas plume detections in a time interval; (iii) determining an emission indicator value based on detection events in a sensor output associated with a sensor of the plurality of sensors at the first unit; and/or (iv) determining, based on corresponding emission indicator values and corresponding response factors for the plurality of sensors, an average emission indicator value for the first unit in the time interval. One or more of steps (i)-(iv) may be optional and/or performed in an order different than enumerated, as appropriate. Similarly, the same or a different one of the one or more emissions monitoring platforms may perform a similar method for the second unit comprising the same one or more aforementioned steps (i)-(iv), but using the plurality of sensors at the second unit and based on at least the gas stream at the second unit. The system may then determine a difference between the average emission value of the first unit in the time interval and the average emission value of the second unit in the time interval. And, then send, to an optional user computing device with a display device, an indication of the difference for display or other output.

BRIEF DESCRIPTION OF THE DRAWINGS

The present disclosure is illustrated by way of example and not limited in the accompanying figures in which like reference numerals indicate similar elements and in which:

FIG. 3 illustrates an example embodiment examples of ionization potentials and response factors for some common gas species, in accordance with various aspects of the disclosure;

FIG. 9 illustrates an example maintenance dashboard, in accordance with various aspects of the disclosure;

Figure 1A:
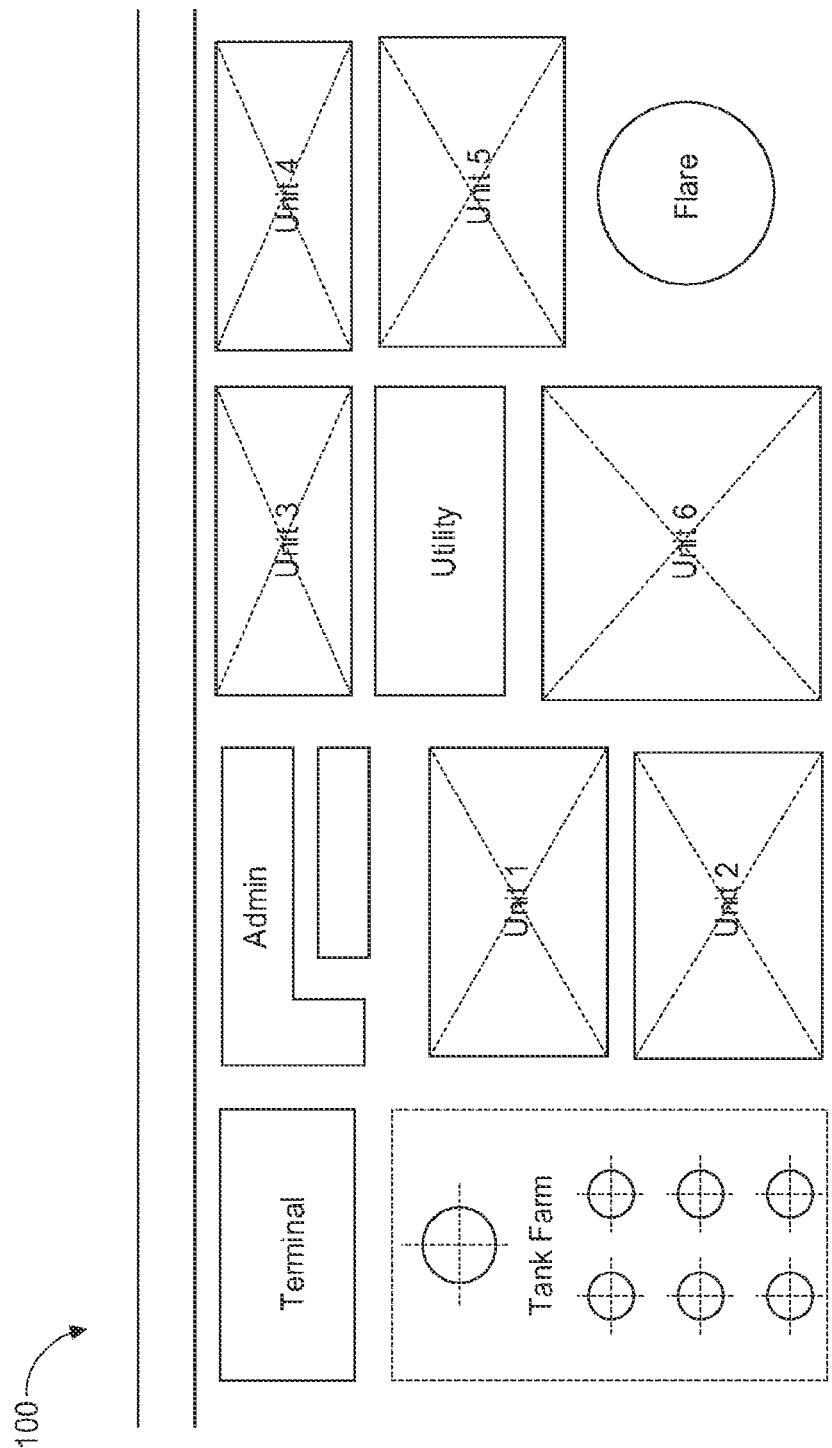
FIG. 1A and FIG. 1B (collectively referred to as "FIG. 1") are illustrations of a representative facility with a sensor network, in accordance with various aspects of the disclosure.

In the following description of various illustrative embodiments, reference is made to the accompanying drawings, which form a part hereof, and in which is shown, by way of illustration, various embodiments in which aspects of the disclosure may be practiced. It is to be understood that other embodiments may be utilized, and structural and functional modifications may be made, without departing from the scope of the present disclosure. It is noted that various connections between elements are discussed in the following description. It is noted that these connections are general and, unless specified otherwise, may be direct or indirect, wired or wireless, and that the specification is not intended to be limiting in this respect.

DETAILED DESCRIPTION

This disclosure describes numerous embodiments involving a monitoring system that collects, analyzes, and/or renders appropriate information about fugitive emissions identified by sensor networks in one or more facilities. Various examples herein describe a network of sensors for gas detection and an emissions monitoring platform, in communication with the network of sensors. In one example, the emissions monitoring platform may comprise a processor, a memory, and/or a communication interface. The processor may process and analyze the data stored in the memory. In some embodiments, the memory may store computer-executable instructions that, when executed by the processor, cause an emissions monitoring platform to perform one or more of the steps disclosed herein. In some embodiments, the emissions monitoring platform may generate emission reports based on values received (e.g., from the one or more sensors) through the communications interface. The emission reports may provide an estimation of fugitive emissions during a particular time interval. Additionally, or alternatively, the emissions reports may provide a comparison between total emissions estimated in multiple different time intervals and/or multiple different facilities.

The emissions monitoring platform may output to a graphical user interface (GUI) on a screen display. The emissions monitoring platform may analyze, filter, and transform collected sensor data into a visual output that is capable of being rendered on a GUI on a screen display. In some embodiments the emissions monitoring platform may include a desktop computer, a smartphone, a wireless device, a tablet computer, a laptop computer, and/or the like. The emissions monitoring platform may be physically located locally or remotely and may be connected by one or more communications links to other devices/systems associated with a facility.

Other embodiments are also disclosed herein involving derivations and combinations of the various method steps and system components disclosed herein. While the disclosure may be susceptible to embodiment in different forms, there is shown in the drawings, and herein will be described in detail, specific embodiments with the understanding that the present disclosure is to be considered an exemplification of the principles of the disclosure and is not intended to limit the disclosure to that as illustrated and described herein. Therefore, unless otherwise noted, features disclosed herein may be combined to form additional combinations that were not otherwise shown for purposes of brevity. It will be further appreciated that in some embodiments, one or more elements illustrated by way of example in a drawing(s) may be eliminated and/or substituted with alternative elements within the scope of the disclosure.

Remote detecting of gas plumes created by component leaks provides an innovative way of monitoring fugitive emissions of VOC compounds—it is faster and more effective in detecting large leaks and controlling total emissions from the plants. Thus, efforts have been put forth to develop sensor network-based emissions monitoring systems that are configured to detect plumes of VOCs, or other gases of interest, within the boundaries of a facility. The monitoring system generally includes sensor nodes placed throughout the facility, meteorological stations, and a data analytics and visualization platform. The sensors are installed in fixed locations throughout the process unit and wirelessly communicate with a central data platform in the cloud, which estimates leak locations by analyzing data with site-specific algorithms. With proper sensor placement, a system can quick detect VOC leaks as low as a few grams per hour as far as 60 ft away from the leak.

Figure 1B:
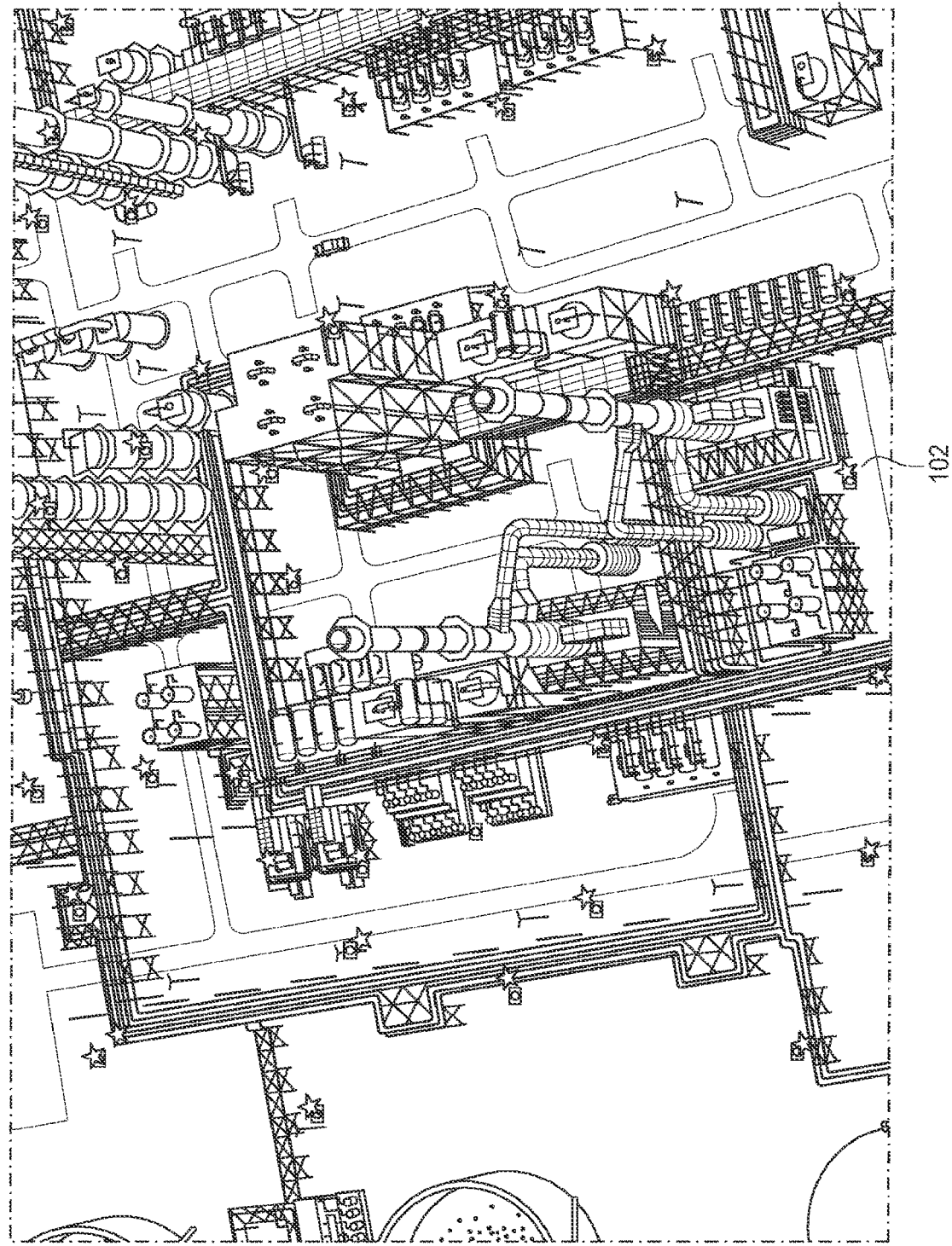

FIG. 1A illustrates a sample two-dimensional layout of a representative facility 100 with a wireless (or wired) sensor network. The facility 100 may comprise multiple LDAR components, such as process units, buildings, etc. (e.g., units 1-6, tank farm, terminal, as shown in FIG. 1A). Gas sensors 102 in the sensor network may be placed in the facility in an optimized way that provides full (or at least substantially full) three-dimensional (3D) detection coverage of LDAR components within a facility, as shown in FIG. 1B. With sensors 102 depicted as stars in FIG. 1B, a higher sensor density may provide better leak detection results or even allow the construction of a dynamic plume profile in a 3D space.

A sensor network may provide a simpler and more reliable solution for conducting LDAR and for monitoring total emissions levels. A network of sensors may be used to detect small plumes created by gas leaks and wind sensors may be used to help triangulate sensor detections to the source of leaks. Multiple sensor nodes may be designed and evenly distributed to provide full coverage of an industrial facility. The sensor system may operate continuously and may be able to detect large leaks from individual components in a timely manner (e.g., within hours/days, as opposed to several months to one year between scheduled inspections based on Method 21). Furthermore, the sensor systems, even if unable to detect individual small leaks from an individual component, may be able to detect a collection of small leaks from a plurality of closely positioned components. The collection of small leaks may be identified by the sensor system as a large leak within an area (e.g., where multiple components may be closely positioned). A component-based approach for estimating/monitoring fugitive emissions, where each component in an industrial facility is independently and manually measured, would no longer be necessary.

A detection zone of a sensor may be depicted by a dot indicating the location of the sensor and a circle to represent the zone within which the sensor may be able to detect a gaseous plume. For simplicity, in some examples, the detection zone of each sensor may be depicted by a circle (or sphere in 3-dimensional representations). However, in other examples, the detection zone may be altered to accommodate the one or more structures, obstructions, and/or openings in the facility. For example, in a 3-dimensional digital representation, the height of an obstructing structure may have direct bearing on sensor placement, specifically whether the height of a structure is such that a sensor placed at a location may be futile to detect a gaseous plume originating from the opposite side of the obstructing structure. Moreover, the detection zone of a sensor may be affected by the type of sensor being used, the sensitivity of the sensor to a particular gas compound, etc.

A wide variety of sensor technologies may be used for gas detection in various examples described herein. Gas sensors may comprise electrochemical sensors, infrared sensors, catalytic bead sensors, metal oxide semiconductor (MOS) sensors, photoionization detectors (PIDs), flame ionization detectors (FIDs), thermal conductivity sensors, colorimetric sensors, sensors based on passive sampling techniques, and/or any other sensors configured to measure concentrations of VOCs and/or other hazardous gases.

Detecting gases in open air requires high sensitivity (typically at concentrations in parts per billion (ppb) level) and fast response times (e.g., due to possible wind and changes in wind speed and direction). Several sensor technologies such as MOS and PID meet the requirements and may be used in fence-line and outdoor air quality monitoring applications.

A PID is equipped with a high energy ultraviolet (UV) lamp and electrodes. Gas molecules with low ionization energy entering a UV chamber in a PID are ionized. Resultant ions flow toward a collecting electrode giving rise to an electric current that is directly proportional to the concentration of the gas. Depending on the target gas to be measured, a PID may use a 9.6 eV, 10.0 eV, 10.2 eV, 10.6 eV, or 11.7 eV lamp. The higher the lamp energy, the more gas species can be measured. A lower energy lamp may be preferred for measurement of aromatic compounds (e.g., benzene) because of better specificity.

Gas sensors have varying sensitivities to different gas species and sometimes need to be calibrated properly before use. A surrogate gas of known concentration may be used to calibrate the sensor. For measuring other gases, a cross-sensitivity factor called response factor may be used to correct a sensor output to provide a measurement. For example, isobutylene is typically used for calibrating PIDs due to its moderate sensitivity and low toxicity. When measuring isobutylene concentration, the calibrated PIDs may directly provide a measurement of the concentration. For other gases, a response factor may be used (e.g., by the emissions monitoring platform 260) for determining the concentration based on measurements provided by the isobutylene-calibrated PIDs.

FIG. 3 shows examples of ionization potentials and response factors for some common gas species. The values in FIG. 3 are one example of data based on PID manufacturer Honeywell's publicly available data; other manufacturers may provide their own data for PIDs, FIDs, MOSs, or other sensors. The example response factors shown in FIG. 3 may correspond to a PID calibrated with isobutylene and using a 10.6 eV UV lamp. The emissions monitoring platform 260 may determine a true gas concentration by scaling a sensor output by the response factor (F) of that gas.

$$\text{Gas Concentration} = \text{Sensor output} \times \text{Response factor } (F) \quad \text{Equation (1)}$$

For example, if the sensor is calibrated with isobutylene and used to measure isobutylene (which has a response factor of 1) then the concentration of isobutylene is considered the same as the sensor reading. If the sensor is used to measure n-octane (which has a response factor value of 1.8) and the sensor output corresponds to a concentration of 10 ppm, then the actual concentration of n-octane is 10 ppm×1.8=18 ppm. If the sensor is used to measure benzene (which has a response factor value of 0.53) and the sensor output corresponds to a concentration of 1 ppm, then the actual concentration of benzene is 1 ppm×0.53=0.53 ppm. Based on equation 1, a low response factor for a gas implies that the sensor is more sensitive to the gas. Conversely, a high response factor for a gas implies that the sensor is less sensitive to the gas. For example, a sensor with response factors given by FIG. 3 is more sensitive to isopropanol than butane.

Many sensor manufacturers provide response factors of different compounds in an instrument built-in software library. When the appropriate response factor is called up (e.g., via a user input), the sensor may determine a true concentration of the compound based on sensor output. Additionally, or alternatively, the emissions monitoring platform 260 may retrieve (e.g., from the data store 290) a response factor to be used for a sensor (e.g., based on sensor location and/or gases that may be present within the detection zone of the sensor) and determine a true concentration based on received sensor output.

For PID sensors, a gas must have an ionization potential below an output energy of the UV lamp in order to be detected. For example, a sensor corresponding to the response factors of FIG. 3 may be unable to detect formaldehyde because the ionization potential of formaldehyde is below the output energy of the UV lamp (10.6 eV).

In an industrial facility, gases may often be present in the form of mixtures. For a gas mixture whose composition is known, an overall response factor F Overall of a sensor for the mixture can be calculated based on response factors of the sensor for each of the component in the mixture. For example, if a gas mixture to be measured by a sensor has n gases, the emissions monitoring platform 260 may determine F Overall as:

$$F_{Overall} = \frac{1}{X_1/F_1 + X_2/F_2 + X_3/F_3 + \ldots + X_n/F_n} \quad \text{Equation (2)}$$

where $X_1$-$X_n$ are the mole ratios of each species in the gas mixture, and $F_1$-$F_n$ are the response factor of the sensor for each species in the gas mixture. The mole ratios of each species of the gas mixture may be retrieved from the data store 290, and/or may be input by a user (e.g., via the user computing device 285). The emissions monitoring platform 260 may determine $F_{Overall}$ based on the mole ratios of the gas mixture and the response factors of the sensor for each of the species. The response factors may be retrieved from the data store 290. The term "gas mixture," as used here for an industrial facility, also contemplates the transport of a gas stream that is composed of just one gas or more than one gas.

Additionally, or alternatively, the emissions monitoring platform 260 may retrieve (e.g., from the data store 290) overall response factors to be used for different sensors. For example, each of the sensors may be associated with a corresponding overall response factor $F_{Overall}$ which may be stored in the data store 290. The emissions monitoring platform 260 may determine an overall response factor for a sensor based on a location of the sensor and/or gases/gas mixtures that may be present within the detection zone of the sensor.

Based on sensor output, the emissions monitoring platform 260 may determine a true concentration of the gas stream/mixture as:

Gas mixture concentration=sensor output×$F_{Overall}$    Equation (3)

For example, a binary gas stream/mixture of equal molar ratios of benzene and n-octane may have an overall response factor $F_{Overall}$ of 1/(0.5/0.53+0.5/1.8)=0.82. A sensor output of 100 ppm would then correspond to actual concentration of 82 ppm of the total mixture (e.g., comprised of 41 ppm of benzene and 41 ppm of n-octane).

For unknown gases or gas mixtures, the sensor may be unable to apply a proper factor or calculate a true concentration. In such cases the sensor output may be deemed to be an "isobutylene-equivalent" response.

Figure 4:
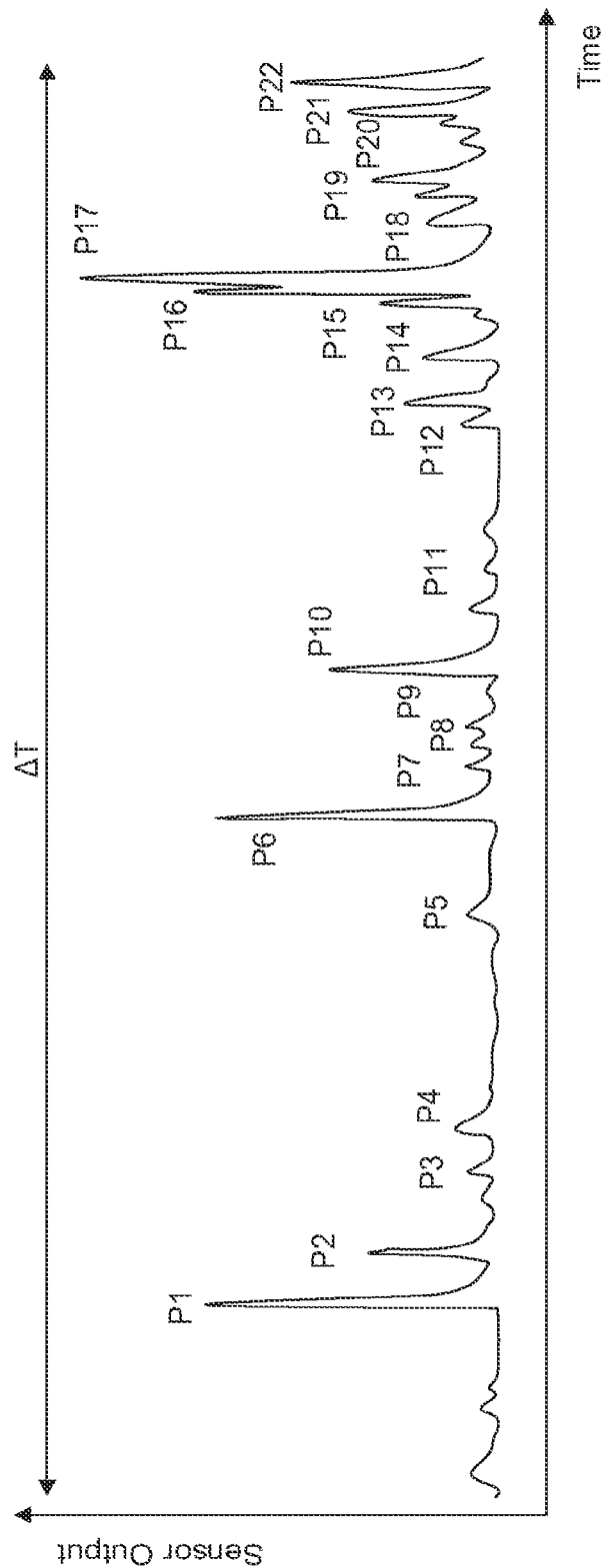
FIG. 4 illustrates output of a sensor over a period of time, in accordance with various aspects of the disclosure.

FIG. 4 illustrates output of a sensor over an about 15-minute period of time. Each peak in the sensor output may be categorized as a sensor detection event and may be a representation of a plume detection. As shown in FIG. 4, a number of peaks (P1-P22) may be identified over a period of time (e.g., time interval $\Delta T$). While the peak height for each peak detection provides a good measure of the signal strength, a peak area may be a better measure of a plume size or emission passing the sensor corresponding to the sensor detection event.

Figure 5B:
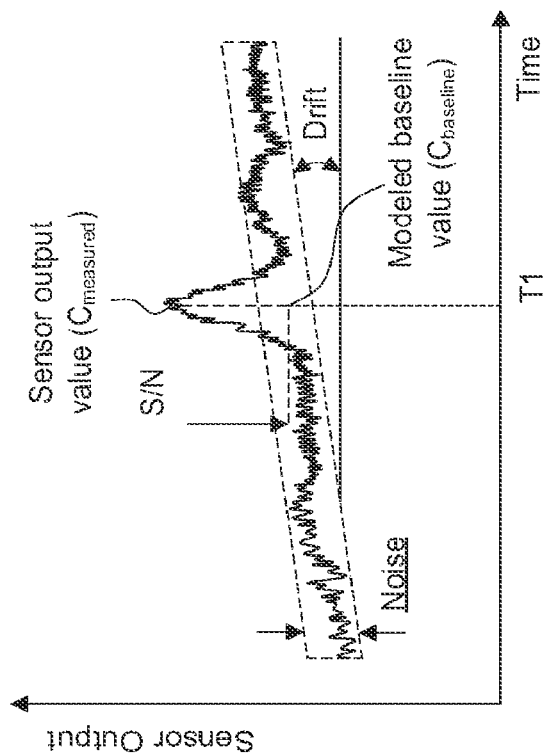
FIG. 5A and FIG. 5B (collectively referred to as "FIG. 5") illustrate an example identification of a peak and a determination of a peak area based on outputs of a sensor, in accordance with various aspects of the disclosure.
Figure 5A:
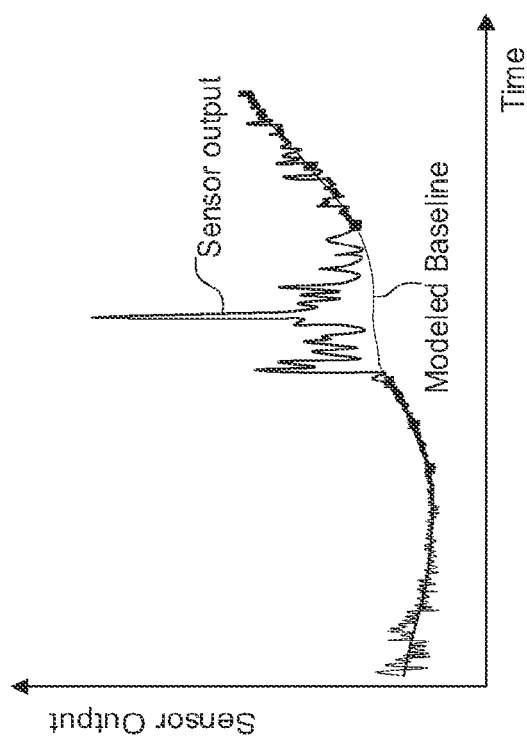

FIGS. 5A and 5B illustrate an example identification of a peak and a determination of a peak area (e.g., by the emissions monitoring platform 260) based on outputs of a sensor. FIG. 5A illustrates an example sensor output over a period of time. The emissions monitoring platform 260 may use a curve-fit model to determine a modeled baseline curve based on the sensor output.

The emissions monitoring platform 260 may identify peaks in determined sensor output over time. The peaks may be identified as sensor output values that exceed a modeled baseline value (e.g., by a threshold). FIG. 5B illustrates an example identification of a peak in sensor output. The emissions monitoring platform 260 may identify a peak at time T1, for example, if a difference between a sensor output value ($C_{measured}$) at time T1 and a modeled baseline value ($C_{baseline}$) at time T1 is greater than a threshold.

The emissions monitoring platform 260 may determine a signal-to-noise (S/N) ratio based on sensor output over a period of time. The threshold may be a multiple of the determined S/N ratio (e.g., two, three, four, twelve, or other value). For example, the emissions monitoring platform 260 may identify a peak at time T1 if:

$C_{measured}$−$C_{baseline}$≥n×S/N ratio    Equation (4)

where n may be any appropriate value (e.g., N=1, 2, 3, etc.), $C_{measured}$ may be the sensor output value at time T1, and $C_{baseline}$ may be a value of the modeled baseline curve at time T1. The emissions monitoring platform 260 may further determine a peak area (s) corresponding to the peak by determining an area under the detected peak and above a modeled baseline.

The emissions monitoring platform 260 may determine an emission indicator value corresponding to a sensor in a time interval. The emission indicator value may be determined based on determined peaks in sensor output values (as observed in the time interval) and peak areas associated with the determined peaks. With reference to FIG. 4, an emission value $S_i$ of the sensor for the time interval $\Delta T$ may be determined based on peak areas corresponding to the individual peaks in the time interval $\Delta T$. For example, if the sensor detects m peaks in the time interval $\Delta T$, the emissions monitoring platform 260 may determine an emission indicator value for the time period $\Delta T$ as:

$$S_i = \sum_{k=1}^{m} s_k \quad \text{Equation (5)}$$

where $s_k$ is a peak area for a detection peak k.

Throughout this application, many gas sensor subject matter concepts are introduced. And innovative algorithms for comparing overall emissions or evaluating changes in overall emissions are illustrated. Based on detection events and particularly sensor detections for a specific time interval and corresponding response factors stored in the archived data, a total emission indicator value for an industrial facility or a specific unit or units within a facility may be calculated by algorithm:

$$D_i = \sum_{i=1}^{n} S_i F_i \quad \text{Equation (6)}$$

where $S_i$ is an accumulative emission detection value for the time interval from sensor i and $F_i$ is an overall response factor for the gas streams at the sensor i, wherein the determining excludes those detection events corresponding to a maintenance activity.

Emission indicator values corresponding to multiple sensors may be aggregated to generate an estimate of emissions over an entire facility. Further, the facility may be associated with a plurality of gases or gas mixtures. A gas stream at a particular location may be known and a response factor/overall response factor for a sensor at the location may be accordingly determined (e.g., based on FIG. 3 or Equation (2)). The emissions monitoring platform 260 may determine a total emission indicator value from all sensors based on individual emission indicator values from the sensors and corresponding response factors/overall response factors associated with the sensors. For example, the emissions monitoring platform 260 may determine a total emission indicator value at a facility (for the time interval $\Delta T$) with n sensors as:

$$D_{total} = \sum_{i=1}^{n} S_i F_i \quad \text{Equation (7)}$$

where $S_i$ is an accumulative emission indicator value (for the time interval $\Delta T$) at sensor i and $F_i$ is a response factor or overall response factor for the sensor i. Additionally, or alternatively, the emissions monitoring platform 260 may determine an average emission indicator value per sensors as:

$$D_{average} = \frac{1}{n} \sum_{i=1}^{n} S_i F_i \quad \text{Equation (8)}$$

$F_i$ may be based on a specific gas or a mixture of gases that the sensor i is measuring. $F_i$ may be based on the gas(es) being processed by specific components/units within a detection zone of the sensor i. For example, the emissions monitoring platform 260 may retrieve (e.g., from the data store 290) $F_i$ corresponding to a sensor based on a location of the sensor and use the retrieved value to determine $D_{total}$ or $D_{average}$.

$D_{total}$ or $D_{average}$ may serve as a general indication of overall emissions in the facility during the time interval T. A higher value of $D_{total}$ may indicate higher total emissions in the facility during the time interval T. A higher $D_{average}$ on the other hand, may indicate a "dirtier" or higher emission rates.

Consider an example facility that handles ethylene and propylene with a total of fifteen sensors distributed evenly. Five sensors may be installed in a propylene storage area and the rest in an ethylene storage area. As shown in FIG. 3, response factors of the sensors for propylene and ethylene may be 1.4 and 9, respectively. The emissions monitoring platform 260 may determine a total emission indicator value $D_{total}$ for this facility as:

$$D_{total} = \sum_{i=1}^{5} 1.4 S_i + \sum_{i=6}^{15} 9 \; S_i$$

Consider another example facility which has 7 units with 200 sensors. Overall response factor for areas covered by sensors 1-40 may be 0.8, overall response factor for areas covered by sensors 41-175 may be 1.5, and overall response factor for areas covered by sensors 176-200 may be 4. The emissions monitoring platform 260 may determine a total emission indicator value $D_{total}$ for this facility as:

$$D_{total} = \sum_{i=1}^{40} 0.8 S_i + \sum_{i=41}^{175} 1.5 S_i + \sum_{i=176}^{200} 4 S_i$$

$\Delta T$ may be adjusted based on use cases of the emissions monitoring system 255. A large $\Delta T$ (e.g., a few months, a year, etc.) may be used to determine total emission levels over large time intervals (e.g., to monitor regulatory compliance) and reduce the influence of transient spikes/other changes in emission level determination. For example, meteorological conditions may affect sensor detection. If there is a sustaining high wind velocity, the sensors are not likely to have large detection due to dilution of gas with wind. Using a larger $\Delta T$ (e.g., a month, three months, or a year) and averaging the detections over $\Delta T$ may minimize these anomalies. On the other hand, a short $\Delta T$ (e.g., in an order of minutes or hours) may be used to estimate emissions in real-time or near real-time and detect immediate issues that may need to be addressed.

Each unit in a facility may be used for processing a specific gas or a specific mixture of gases. The emissions monitoring system 255 may be configured to not only determine total emission indicator value but also specific emission indicator value for an individual gas or gas mixture. For determining a specific emission indicator value for an individual gas or gas mixture, the emissions monitoring platform 260 may aggregate emission indicator values from sensors which have, within corresponding detection areas, units that process the gas or gas mixture. Returning to the example facility that handles ethylene and propylene with a total of fifteen sensors with five sensors installed in a propylene storage area and the rest in an ethylene storage area, the emissions monitoring platform may determine specific emission indicator value for propylene based on sensor outputs from the five sensors in the propylene storage area. The emissions monitoring platform 260 may determine a specific emission indicator value $D_{propylene}$ for this facility as:

$$D_{propylene} = \sum_{i=1}^{5} 1.4 S_i$$

The data store 290 may store associations between sensors and corresponding gases within detection zones of each of the sensors. The emissions monitoring platform 260 may select sensors to be used for determining a specific emission indicator value for a gas/gas mixture based on the association.

Emission levels may be determined, monitored, and compared using a sensor network (e.g., gas sensor(s) 265A) in functional operation with, for example, a software platform at the emissions monitoring platform 260 and/or the user computing device 285). The software platform may present a GUI (e.g., at the user computing device 285) which may be used to receive input parameters and display an output based on various calculations described herein.

Various values determined by the emissions monitoring platform 260 may be viewed via a GUI on a display device associated with the user computing device 285. For example, as described herein, the sensors may provide sensor output values to the emissions monitoring platform 260. The emissions monitoring platform 260 may determine, based on the sensor output values, true gas/gas mixture concentrations, emission values, total/average emission indicator values, and/or specific emission indicator values. Values determined by the emissions monitoring platform 260 may be sent to the user computing device 285 and may be viewed, via a GUI, on a display at the user computing device 285.

Conventional techniques may rely only on a quantity of leaks detected in a facility (e.g., a quantity of sensors detecting leaks) to determine an extent of fugitive gas emissions in the facility. However, this may not necessarily accurately quantify an extent of the fugitive gas emissions. Quantitative determination of total emission levels as described herein may enable accurate tracking of fugitive gas emissions and enable corrective actions to be taken based on sensor measurements. For example, repairs may be prioritized in detection zones corresponding to sensors that report high emission values.

Figure 6B:
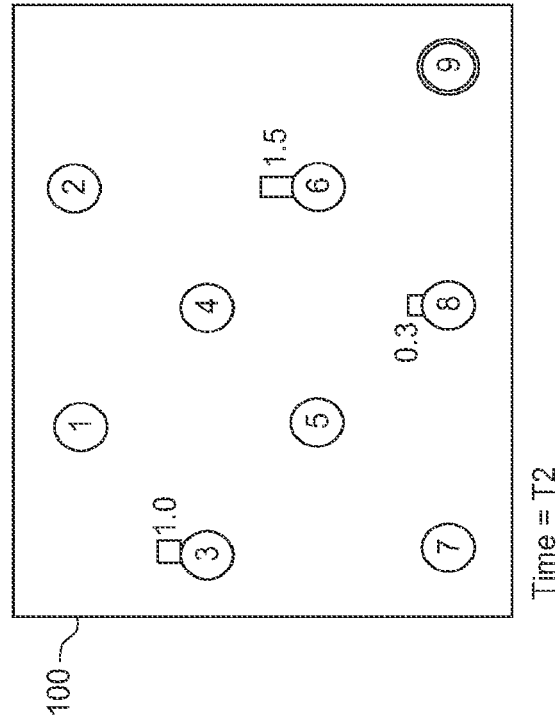
FIG. 6A and FIG. 6B (collectively referred to as "FIG. 6") illustrate an example operation of an emissions monitoring system, in accordance with various aspects of the disclosure.
Figure 6A:
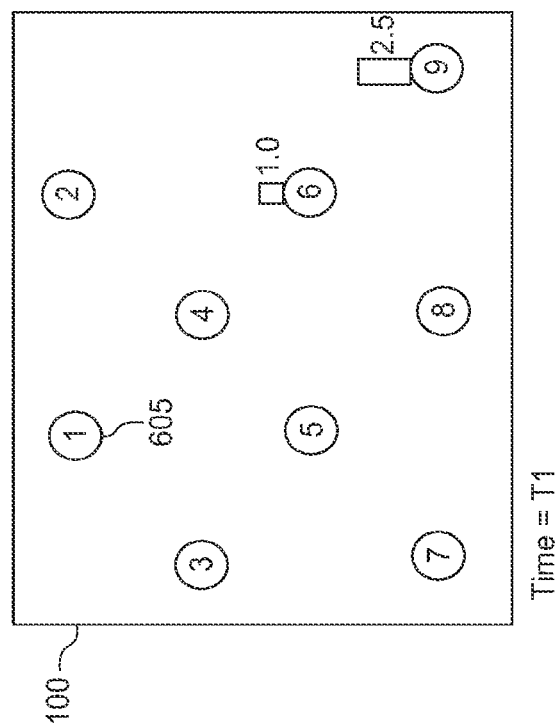

FIGS. 6A and 6B illustrate an example operation of an emissions monitoring system. The emissions monitoring system may correspond to a facility comprising nine sensors. FIGS. 6A and 6B show example output values for each of the sensors 605 determined based on measurements by the sensors 605. The example output values shown in FIGS. 6A and 6B may be determined by Equation (7) with corresponding response factors or overall response factors for the sensors (e.g., a product of $S_i$ and $F_i$). A total emission value for the facility 100 may be equal to an aggregate of the output values for each of the sensors 605. FIG. 6A shows example output values as determined at time T1, and FIG. 6B shows example values at time T2.

As shown in FIG. 6A, at time T1, the emissions monitoring platform 260 may detect one or more leaks in detection zones of sensor 6 and sensor 9. The emissions monitoring platform 260 may determine output values for sensor 6 and sensor 9 to be equal to 1 and 2.5, respectively. Output values for the other sensors may be equal to 0. Therefore, a total emission indicator value at time T1 may be equal to 3.5. Based on determining the leaks in the detection zones of sensor 6 and sensor 9, corrective actions may be taken. For example, at least a leak in a unit in a detection zone of sensor 9 may be fixed. The facility may prioritize repairs in the detection zone of sensor 9 based on higher emission values reported by sensor 9. For example, the emissions monitoring platform 260 may send an alert to the user computing device 285 indicating a potential leak source around sensor 9.

As shown in FIG. 6B, at a later time T2, the emissions monitoring platform 260 may detect leaks in detection zones of sensor 3, sensor 6, and sensor 8. Time T2 may be after the time T1 and may correspond to a time following the repair in the detection zone of sensor 9. The emissions monitoring platform 260 may determine emission indicator values for sensor 3, sensor 6, and sensor 8 to be equal to 1, 1.5, and 0.3, respectively. Emission indicator values for the other sensors may be equal to 0. A total emission indicator value at time T2 may therefore be equal to 2.8. Based on a comparison between total emission indicator values at time T1 and total emission indicator values at time T2, the emissions monitoring platform 260 may accurately determine that the total fugitive gas emissions have reduced in the facility 100, even though a number of sensors that have detected leaks may have increased. This may provide a better representation of an extent of fugitive gas emissions as compared to a system that merely tracks a number of sensors that have detected leaks.

The emissions monitoring platform 260 may communicate with sensors and/or other emissions platforms (e.g., via the wide area network 275) at other facilities to perform a comparison between emission indicator values/total emission indicator values determined across multiple facilities. For example, the emissions monitoring 260 may determine total emission indicator value (e.g., in a time interval) for two different facilities, perform a comparison between the two, and provide the result to the user computing device 285. The user computing device 285 may display (e.g., in a GUI) results of the comparison. This may enable a user to determine and compare performance of various interconnected facilities via a single interface.

The emissions monitoring platform 260 may be configured to provide a comparison between total emission indicator values (or average emission indicator values) determined for two different time intervals. For example, a user may input time intervals (e.g., via the user computing device 285) for which a comparison is to be performed. Based on various calculations performed by the emissions monitoring platform 260 (as described above), the user computing device 285 may provide a GUI displaying a result of the comparison.

An emissions indicator value may be used in a variety of applications, including but not limited to, comparing emissions from different time periods, comparing emissions from different units in one facilities, comparing emissions likelihood based on operations and maintenance procedures of different units, comparing emissions levels using the average emissions indicator value per sensor which may suggest one unit or facility is "cleaner" than the other, and/or combination thereof. In some examples, when emissions from maintenance or authorized emissions are included the calculation, government agencies or research organizations may use these data to evaluate emissions levels in different geographic areas for air quality control and/or climate change studies. The disclosure is not limited to the aforementioned examples; a person of ordinary skill in the art after review of the entirety disclosed herein will recognize that the disclosure contemplates other use cases derived from the features disclosed herein.

Figure 7:
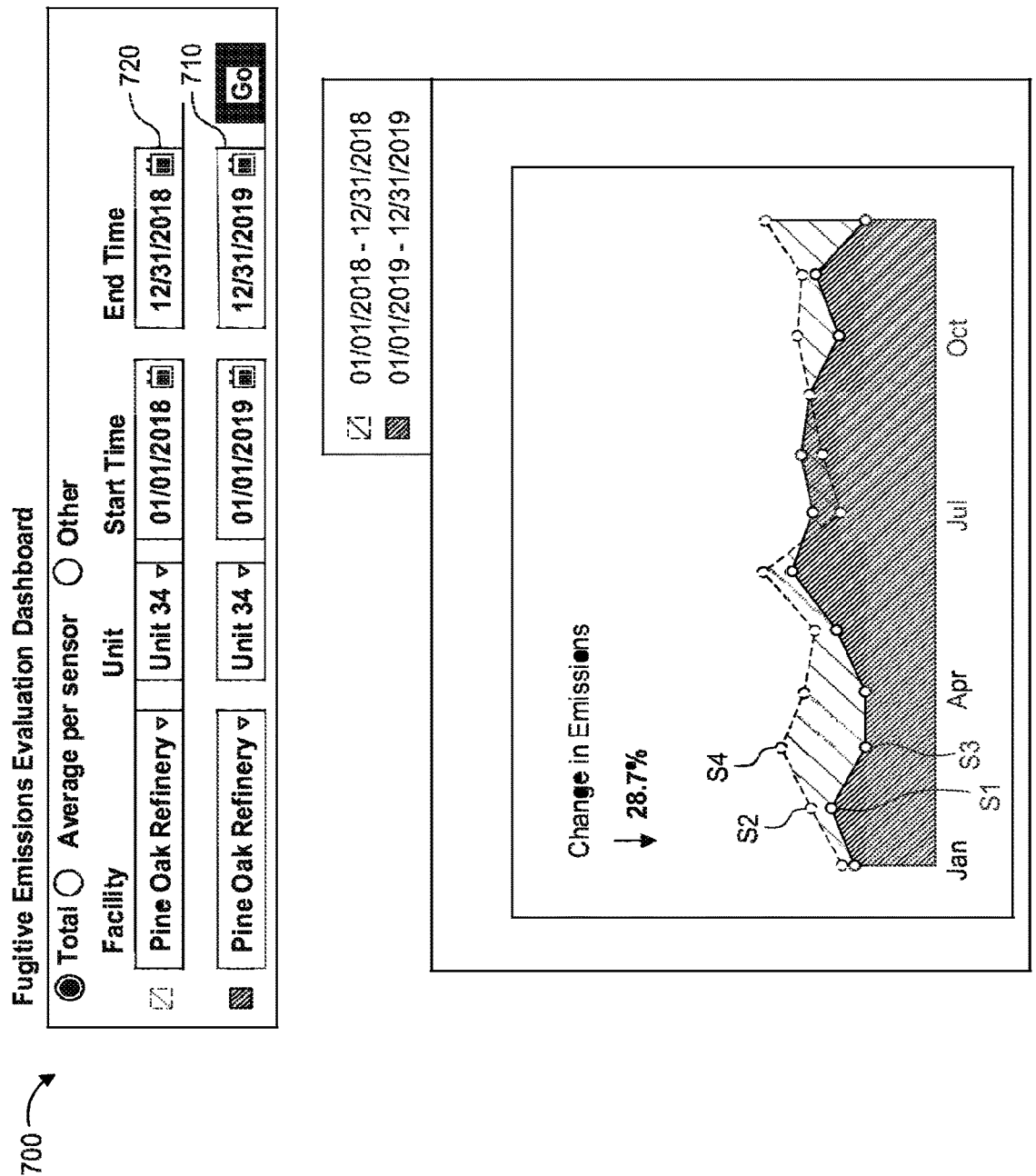
FIG. 7 illustrates an example GUI that may be displayed on a user computing device, in accordance with various aspects of the disclosure.

FIG. 7 illustrates an example GUI 700 that may be displayed on the user computing device 285 to provide an intuitive interface for comparison and/or evaluation of emissions. FIG. 7 illustrates one graphical depiction of a fugitive emission evaluation dashboard disclosed herein. On the dashboard GUI, a user may pick an evaluation method, a facility, and/or a unit from a drop-down list and identify a particular time period 710, 720 for comparison. Results are then displayed numerically and/or graphically including details over the whole specified time period. While this analysis may be started manually on the dashboard, in one example, it is not uncommon to run an analysis of interest by default. In one example, a user may choose to set up a display of the trends in total emissions and keep it updated with time on the system summary/overview dashboard. In some examples, the fugitive emissions evaluation data may be combined with other data on the platform or data from the plant information (PI) system to conduct a holistic analysis and trade-off across operation, safety, and emissions control of the industrial facility to provide ongoing improvement across operations lifecycle.

The GUI 700 may be displayed based on various analyses performed by the emissions monitoring platform 260. The GUI 700 shows a comparison between total emission indicator values determined in two different years. Each point on the line 710 represents total emission indicator values, for a current year, as determined based on sensor measurements performed over a time interval comprising 12 months prior to the point. Each point on the line 720 represents total emission indicator values, for a previous year, as determined based on sensor measurements performed over a time interval (e.g., 12 months, 3 months, 6 months, or other time period).

For example, a total emission indicator value S1 for February of a current year may be determined based on sensor measurements received over a time interval comprising 12 months prior to February of the current year. A total emission indicator value S2 for February of the previous year may be determined based on sensor measurements received over a time interval comprising 12 months prior to February of the previous year. Similarly, a total emission indicator value S3 for March of the current year may be determined based on sensor measurements received over a time interval comprising the 12 months prior to March of the current year. A total emission indicator value S4 for March of the previous year may be determined based on sensor measurements received over a time interval comprising 12 months prior to March of the previous year.

With reference to FIG. 7, total emission indicator values may be determined with a granularity of a month, but any other granularity may be used (e.g., a day, a week, etc.). The emissions monitoring platform 260 may determine, based on a plurality of total emission indicator values, aggregated total emission indicator values, which may be used for further analyses and monitoring. For example, with reference to FIG. 7, the emissions monitoring platform 260 may determine an overall change in emissions by: determining a first aggregated total emission indicator value by aggregating total emission indicator values for each month of the current year, determining a second aggregated total emission indicator value by aggregating total emission indicator values for each month of the previous year, and determining a difference between the first aggregated total emission indicator value and the second aggregated total emission indicator value. For example, FIG. 7 shows that emissions determined for the current year are down 28.7% as compared to emissions determined for the previous year.

Various parameters to be used for determining total emission indicator values, performing emissions comparisons, and displaying a GUI (e.g., the GUI 700) may be based on user input at the user computing device 285. For example, the user may input a value for a length of time interval to be used, indications of sensors to be used for determining the emission indicator values and performing the comparison, a granularity of comparison, times for which a comparison is to be performed, etc. With reference to the GUI 700, for example, the user computing device 285 may display the GUI 700 based on a user input indicating that a comparison is to be performed for total emission indicator values as determined for two years, with a granularity of one month, and a length of a time interval equal to 12 months.

One or more units (or parts of a unit) in a facility may be shut down to perform maintenance. Maintenance may include various activities related to protection, repair, and/or restoration of equipment in order to maintain function and integrity. Typical maintenance activities may include cleaning, inspection, lubrication, testing, replacing, and/or repairing components. A constantly operating pump, for example, may present risks of fire and may need to be checked/tuned up regularly. Pipes and vessels handling heavy oil, for example, may need regular cleaning to prevent build-up of solid residues over time. Maintenance activities may last from a few hours to a few weeks.

There may be significant or insignificant emissions during each maintenance activity. However, in one example, these emissions are authorized emissions under current regulations, which means they do not need to be reported and/or included in the final, total quantity reported to the state or federal environmental protection agencies. Sensors in an area subject to maintenance related emissions may show substantially higher sensor outputs, which may skew the total emission indicator values in the facility and may result in inaccurate emissions calculations and improper comparisons for regulatory compliance purposes. To avoid this, measurements obtained during a maintenance activity may be excluded from calculations of the total emission indicator value. For example, the emissions monitoring platform 260 may exclude sensor outputs, from all sensors in the facility, that are determined to be impacted during the maintenance activity. Alternatively, the emissions monitoring platform may exclude sensor outputs, corresponding to sensors which have detection zones that overlap with areas that may be subject to maintenance related emissions during the maintenance activity. Excluding sensors outputs may comprise ignoring any detection events (e.g., peaks) that may be recorded in sensor outputs during the maintenance related activity.

Figure 8:
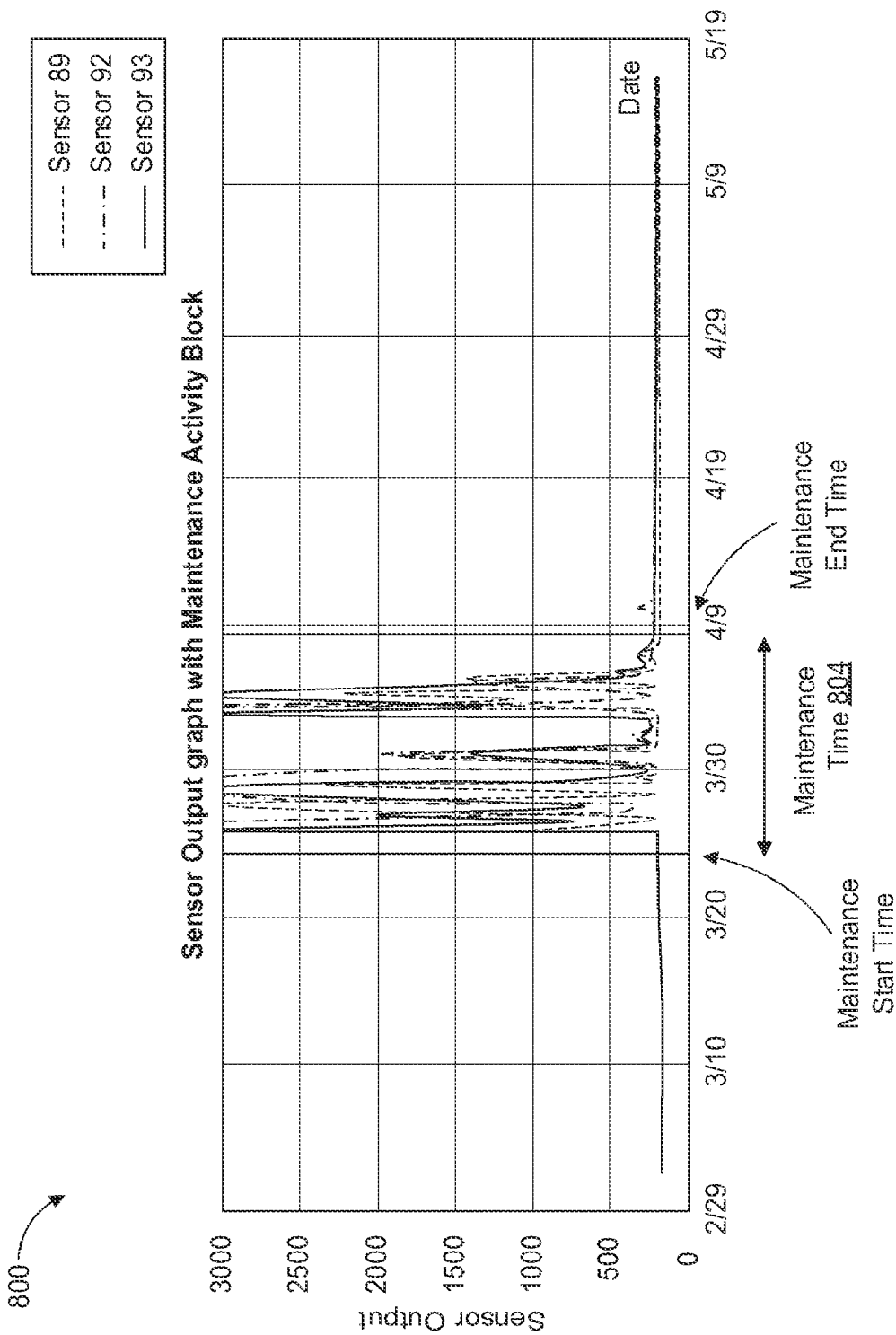
FIG. 8 illustrates example sensor outputs as observed over a time interval, in accordance with various aspects of the disclosure.

FIG. 8 illustrates example sensor outputs 800 as observed over a time interval. The time interval may include time corresponding to a maintenance activity. The sensor outputs correspond to three sensors that may be in an area that is subject to maintenance activities during a maintenance time 804. As illustrated in FIG. 8, the sensors may record a high sensor output during the maintenance time 804 and may skew total emission values that may be calculated for a time interval that may include the maintenance time 804. To avoid this, the emissions monitoring platform 260 may, for calculating the total emission indicator values, exclude any sensor outputs (e.g., detection events) from the three sensors during the maintenance time. Alternatively, the emissions monitoring platform 260 may exclude any detection events that may be recorded by any sensor in the facility during the maintenance time.

A software platform in the emissions monitoring system 255 may be used to document the maintenance activities. Each maintenance activity may be associated with a specific time window, specific unit(s)/component(s) within the facility, and/or sensor(s) that may be impacted. A user may input (e.g., via the user computing device 285) maintenance activity information to the system before/after each maintenance activity with starting time, ending time, specific location or area and nature of activity. Once the maintenance activity information is added, any plume detections (peaks) recorded by the sensors during that time window may be excluded from total emissions calculation. The exclusion time may be prorated by the software platform in order to make valid comparisons for the same period of time. In one example, a unit was running only 9 months (January 1-September 30) this past year due to a major construction work, but it was fully operating the year before. In order to compare emissions levels of these two years, the emissions monitoring platform may calculate the average monthly emission indicator value of this past year over the 9 operating months and multiply the monthly average by a factor of 12 to obtain an estimation for the whole year, and then use this number to compare with that of the prior year. Alternatively, the emissions monitoring platform 260 may only use the 9-month emission indicator data calculated from this year to compare with the 9-month data for the same time period January 1 to September 30 of the prior year.

In another example, emissions calculations and/or comparison may be performed with all the detections including detections during a maintenance period (e.g., for research and/or documentation purposes. For example, a plant may want to monitor total emissions associated with a particular maintenance task. A research organization may compare total emissions in two or more geographic regions for air quality or climate change studies, etc.

FIG. 9 illustrates an example maintenance dashboard 900, based on user input, which may be used to document maintenance activities in a facility. The maintenance dashboard 900 may record maintenance activities that are scheduled for the future, are being currently being performed, and/or have already been completed. Each maintenance activity may be associated with unit(s) 902 in the facility that are subject to the maintenance activity, a maintenance start date/time 904, a maintenance end date/time 906, a work description 908 associated with the maintenance activity, and sensors 910 that are affected by the maintenance activity. As described above, a user may input at least some of the information in the maintenance dashboard (e.g., via the user computing device 295).

The dashboard 900 described here involves post-processing of archived data. The post-processing is a data operation performed in a server computer in the cloud or network initiated from the software platform, manually or automatically. Various embodiments disclosed herein may be used as an add-on feature on a fugitive emission monitoring software platform, while the system itself may collect, stream, and process sensor data from the field (e.g., of an industrial facility) and provide real-time/near real-time feedback including, but not limited to severity of leakage and potential leak source locations. In some embodiments, the system may further manage sensor health data and detection notifications and investigations conducted under each notification. The post-processing of sensor data in this application may be performed independently from the real-time features, and it may analyze archived data or data collected in the past time period. It doesn't interfere with the operation or affect the real-time performance of the sensor network system in the detection of gas leaks in the field. The archived data may be historical data from prior years, months, days, hours, or other time period that is stored in a data store accessible to the server computer in the software platform.

Data input via the maintenance dashboard 900 may be stored in the data store 290 and may be used by the emissions monitoring platform 260 to perform various analyses described herein. For example, the emissions monitoring platform 260 may ignore (e.g., not include) any detection events recorded by any sensor in the facility for calculation of emission indicator values and/or total detected emissions (e.g., as described with reference to Equations (5) and (6)). Alternatively, the emissions monitoring platform 260 may ignore (e.g., not include) any detection events recorded by a sensor associated with a maintenance activity for calculation of emission indicator values and/or total detected emissions. For example, with reference to maintenance activity 912, the affected sensors are S-17, S-20, and S-30. The emissions monitoring platform 260 may ignore any detection events recorded by the sensors S-17, S-20, and S-30 during the maintenance time corresponding to the maintenance activity 912. In another example, the emissions monitoring platform 260 may ignore any detection events recorded by any sensor in the facility during the maintenance time corresponding to the maintenance activity 912.

While the above examples illustrate the use of a maintenance dashboard to record maintenance activities and determine emission indicator values and/or total detected emissions, maintenance activities may be determined based on locations associated with employees in the facility. For example, each employee may be equipped with a location tracking device (e.g., a global navigation satellite system (GNSS) tracker, a smartphone with built-in tracking capabilities, or any other tracking device) that may be used to determine an employee location. The emissions monitoring platform 260 may assume/determine that a unit in the facility is subject to maintenance activities, for example, if an employee is located in a proximity of the unit. The emissions monitoring platform 260 may further determine one or more sensors with detection zones that may comprise the unit. Any detection events recorded by the one or more sensors may be ignored (e.g., for the duration of time that the employee is located in the proximity of the unit) by the emissions monitoring platform 260 for determination of emission indicator values and/or total emission indicator values. For example, the emissions monitoring platform 260 may exclude any detection events that may be detected by a sensor, for example, if an employee is detected in a proximity of sensor or in a proximity of unit within a detection zone of the sensor.

Figure 10:
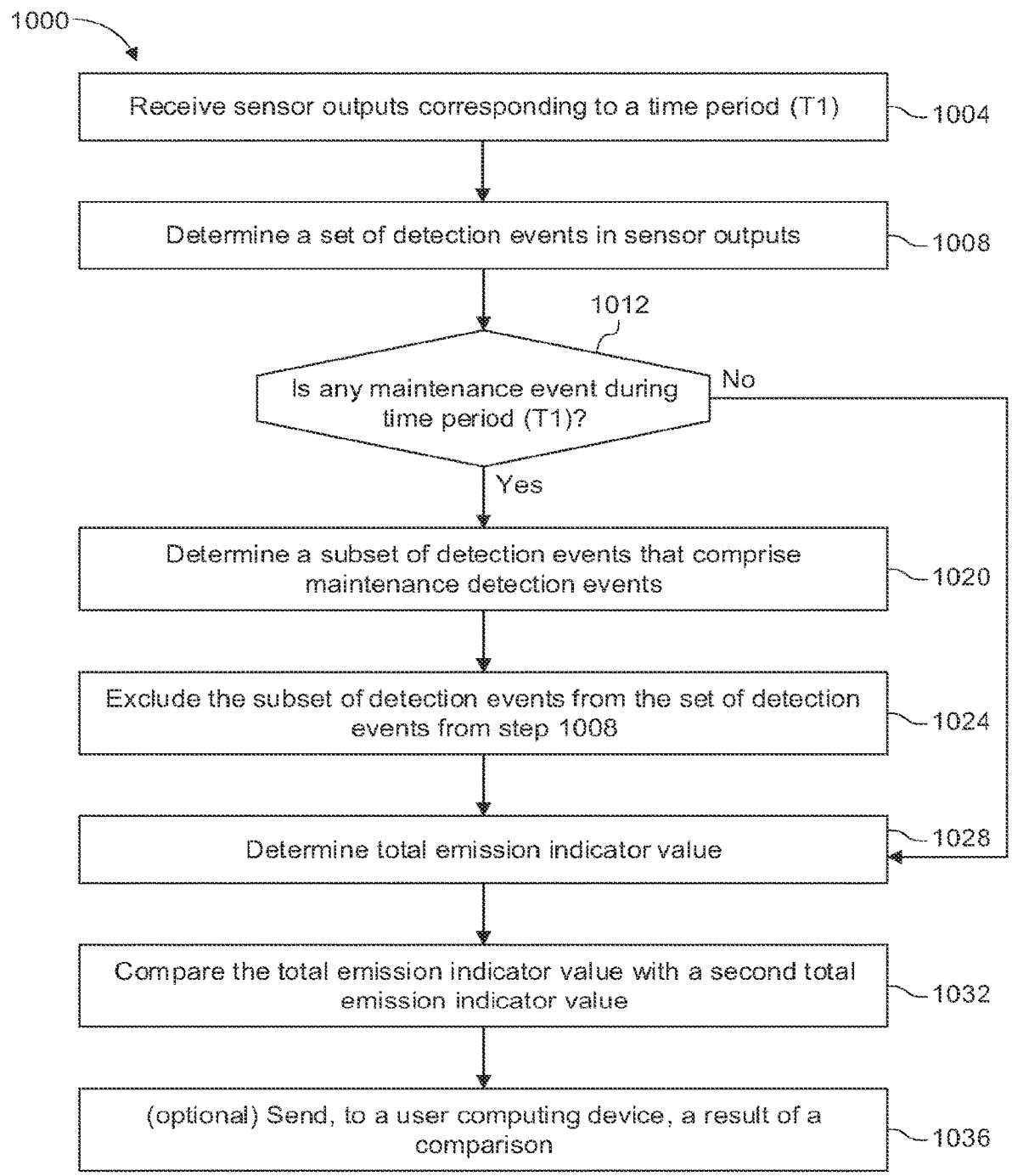
FIG. 10 is an illustrative flowchart of a method of monitoring fugitive gas emissions, in accordance with various aspects of the disclosure.

FIG. 10 illustrates an example method 1000 of monitoring fugitive gas emissions. In an arrangement, the example method 1000 may be performed by an emissions monitoring platform (e.g., the emissions monitoring platform 260). At step 1004, the emissions monitoring platform may receive sensor outputs from a plurality of sensors (e.g., the gas sensors 265A) in a facility. The sensor outputs may correspond to measurements by the sensors in a specified time interval. At step 1008, the emissions monitoring platform may determine a set of detection events in the sensor outputs. At step 1012, the emissions monitoring platform may determine if any subset of detection events (in the set of detection events) corresponds to any maintenance time at one or more units in the facility 100.

At step 1020, the emission monitoring platform 260 determines if a subset of detection events (in the set of detection events) corresponds to a maintenance time. As explained in this disclosure, an updated set of detection events may be determined, based on the set of detection events, by excluding (in step 1024) the subset of detection events from the set of detection events that correspond to times when a maintenance activity was being performed in a particular area/region of the facility 100. In one example, at step 1024, the emissions monitoring platform 260 may determine emission indicator values (e.g., using Equation (5)) for each sensor based on the updated set of detection events. If a subset of detection events (in the set of detection events) do not correspond to a maintenance time, the emissions monitoring platform may determine emission indicator values for each sensor based on the full set of detection events without excluding a subset of detection events.

At step 1028, the emissions monitoring platform may determine a total emission indicator value (e.g., using Equation (6)) based on the determined emission indicator values for each sensor. As previously explained, the calculated total emission indicator value is based on one or more detection events that do not correspond to a maintenance event, as illustrated in FIG. 10. Thus, the emissions monitoring platform is repeatedly reviewing the set of detection events to determine which ones should be included into the total emissions indicator value calculation. At step 1032, the emissions monitoring platform may compare the determined total emission indicator value with a second total emission indicator value. For example, the second total emission indicator value may be determined based on sensor outputs in a second specified time interval. As another example, the second total emission indicator value (or average emission value) may be determined based on sensor outputs at a different facility (e.g., in the specified time interval). At step 1036, the emissions monitoring platform may optionally send, to a user computing device, a result of the comparison. The user computing device may display a GUI based on the comparison. For example, the GUI may indicate the total emission indicator value (or average emission value), the second total emission indicator value (or second average emission value), and/or a difference (e.g., relative emission) between the two.

Figure 11:
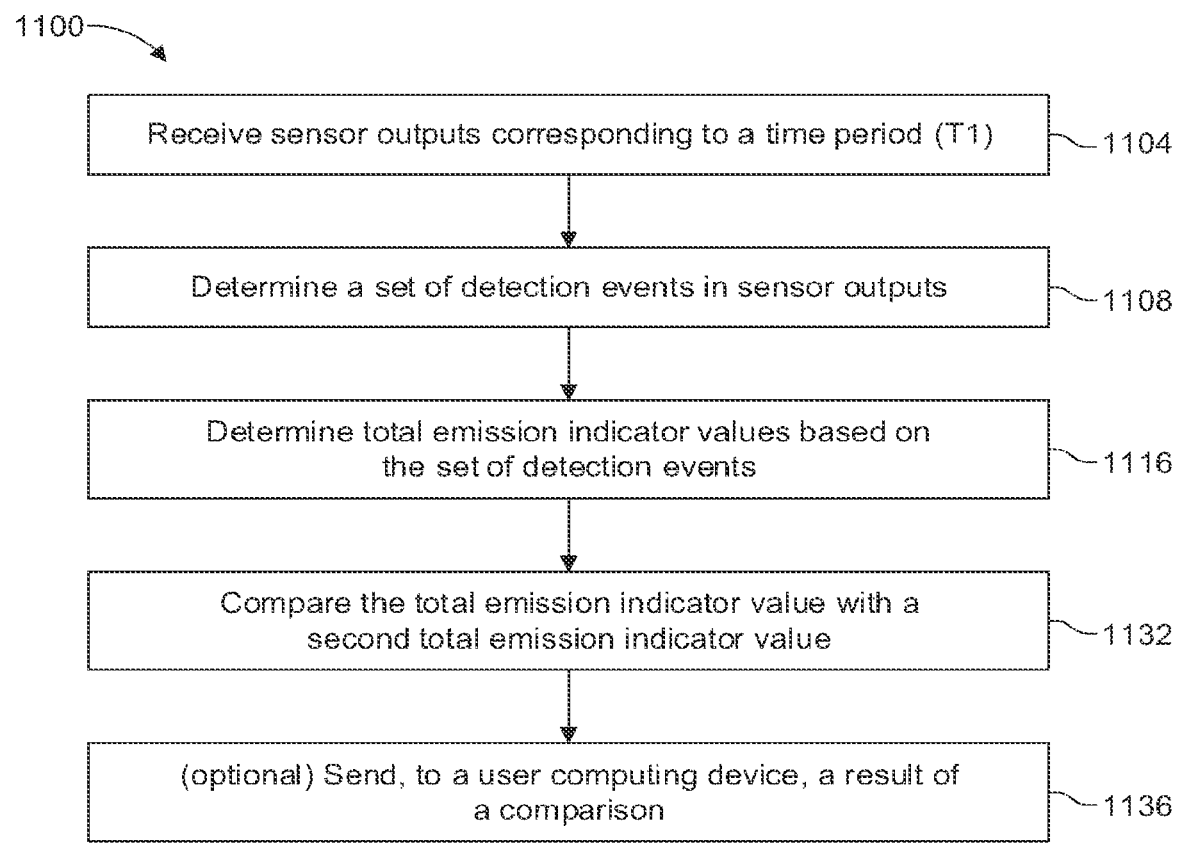
FIG. 11 is an illustrative flowchart of another method of monitoring fugitive gas emissions, in accordance with various aspects of the disclosure.

FIG. 11 illustrates another example method 1100 of monitoring fugitive gas emissions. In an arrangement, the example method 1100 may be performed by an emissions monitoring platform (e.g., the emissions monitoring platform 260). At step 1104, the emissions monitoring platform may receive sensor outputs from a plurality of sensors (e.g., the gas sensors 265A) in a facility. The sensor outputs may correspond to measurements by the sensors in a specified time interval. At step 1108, the emissions monitoring platform may determine a first set of detection events in the sensor outputs. At step 1116, the emissions monitoring platform may determine a total emission value (e.g., using Equation (7)) based on the determined emission indicator values for each sensor. At step 1132, the emissions monitoring platform may compare the determined total emission indicator value with a second total emission indicator value. For example, the second total emission indicator value may be determined based on sensor outputs in a second specified time interval. As another example, the second total emission indicator value may be determined based on sensor outputs at a different facility (e.g., in the specified time interval). At step 1136, the emissions monitoring platform may send, to a user computing device, a result of the comparison. The user computing device may display a GUI based on the comparison. For example, the GUI may indicate the total emission indicator value, the second total emission indicator value, and a difference between the two.

Various examples herein describe monitoring of total emissions in a facility (e.g., in real-time or near real-time) and/or comparing emission levels in different time intervals and/or across multiple different facilities. Various examples herein describe methods, apparatuses, and systems for determining changes or trends in total emissions for a facility or specific units within a facility. Information provided for an emissions monitoring system as described herein may be used, for example, to: (a) evaluate change in total emissions levels from a facility in a timely manner; (b) evaluate consistency of the LDAR sensor solutions over time; and/or (c) evaluate effectiveness of established LDAR training programs.

Figure 2:
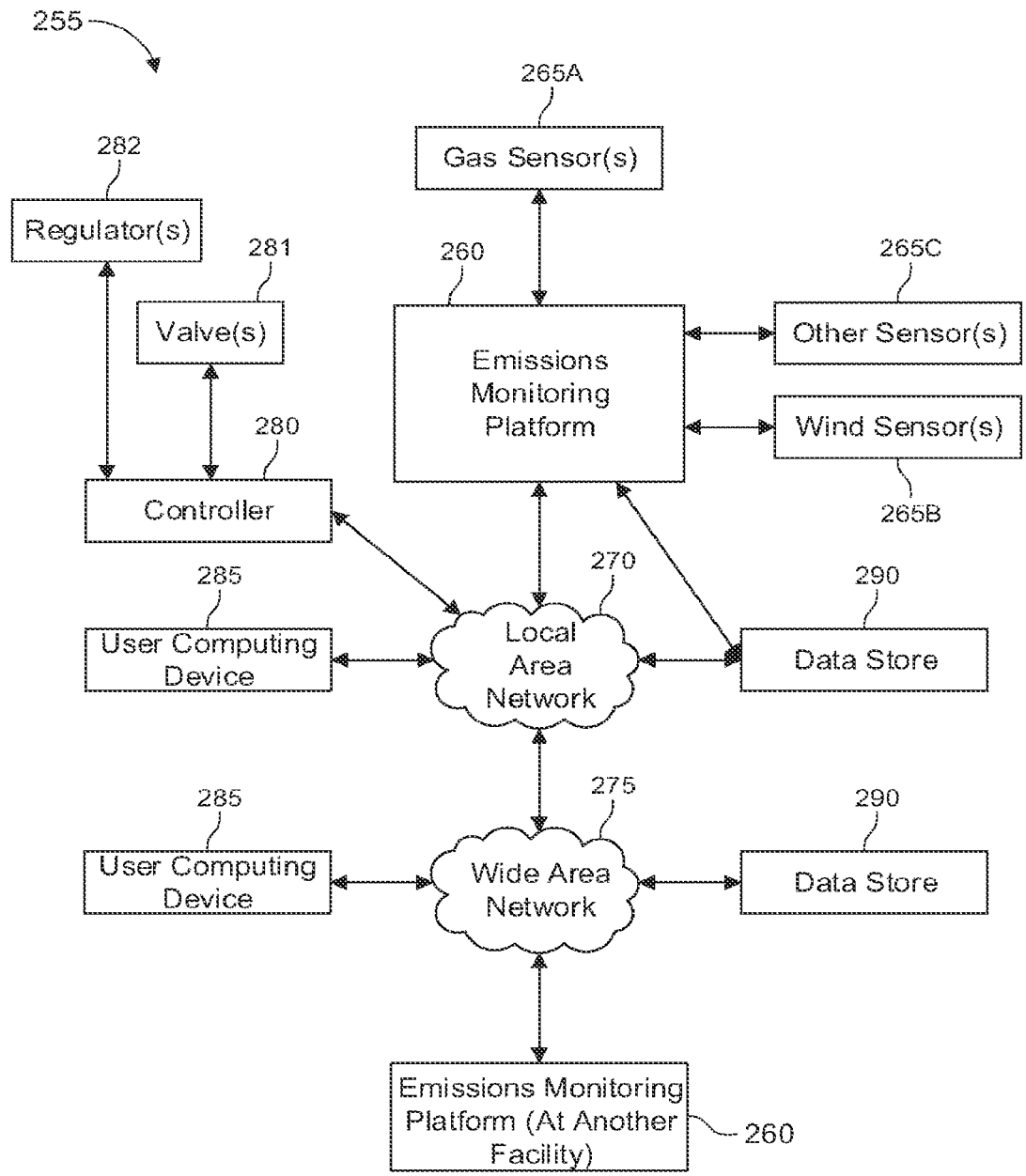
FIG. 2 illustrates an example embodiment a block diagram of a sensor network-based emissions monitoring system, in accordance with various aspects of the disclosure.

For example, FIG. 2 illustrates a block diagram of another example of a sensor network-based emissions monitoring system 255 which is used, in whole or in part, to perform the methods described herein. The disclosure is not limited to just the combination of elements depicted in FIG. 2; rather, numerous variations of the sensor network-based emissions monitoring system are contemplated by the method steps, apparatus components, system interactions, and other aspects disclosed herein. For example, the emissions monitoring platform 260 may be communicatively coupled with one or more sensors, such as gas sensor(s) 265A, wind sensor 265B, and/or one or more other sensors 265C such as a GPS location sensor. In one example, one transmitter may carry multiple sensors of one or more types. For example, a single sensory assembly may comprise multiple sensors of one or more types. In another example, a networked sensor may comprise multiple sensors of more than one type. The sensors may operate to collect measurements in near real-time for input to the emissions monitoring platform 260.

The emissions monitoring system 255 of FIG. 2 includes block diagrams of numerous platforms and devices that are further elaborated in this disclosure. FIG. 2 is an illustrative emissions monitoring system with one or more processing apparatuses to implement the methods and functions of certain aspects of the present disclosure. The processing apparatuses may include general-purpose microprocessors and/or special-purpose processors designed for particular computing system environments or configurations. For example, the processors may execute computer-executable instructions in the form of software and/or firmware stored in the memory of the platform or device. Examples of well-known computing systems, environments, and/or configurations that may be suitable for use with the disclosed embodiments include, but are not limited to, personal computers (PCs), server computers, hand-held or laptop devices, smart phones, multiprocessor systems, microprocessor-based systems, programmable consumer electronics, network PCs, minicomputers, mainframe computers, distributed computing environments that include any of the above systems or devices, and the like.

In addition, the platform and/or apparatuses in FIG. 2 may comprise one or more memories, such as any of a variety of computer-readable media. Examples of computer-readable media may include tangible computer memory accessible to an emissions monitoring platform 260. The memory may be non-transitory, volatile or nonvolatile, and/or removable and non-removable media implemented in any method or technology for storage of information, such as computer-readable instructions, object code, data structures, database records, program modules, or other data. Examples of computer-readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by emission monitoring platform 260. The memories may further include data store 290 in the platform and may further store modules that may include compiled software code that causes the platform, device, and/or overall system to operate in a technologically improved manner as disclosed herein. For example, the data store 290 may store software used by a computing platform, such as operating system, application programs, and/or associated database.

Furthermore, the devices in FIG. 2 may include one or more communication interfaces including, but not limited to, a microphone, keypad, touch screen, and/or stylus through which a user of a computer (e.g., user computing device 285) may provide input, and may also include a speaker for providing audio output and a video display device for providing textual, audiovisual and/or graphical output. The communication interfaces may include a network controller for electronically communicating (e.g., wirelessly or wired) over a public network 275 or a private network 270 with one or more other components on the network. The network controller may include electronic hardware for communicating over network protocols, including TCP/IP, UDP, Ethernet, and/or other protocols. In some examples, the emissions monitoring platform 260 may be a cloud-based device that operates remote from the facility over a computer network.

Controller 280 may interact with and/or execute commands received from an emissions monitoring platform 260. The controller 280 may be communicatively coupled to the emissions monitoring platform 260 and configured to actuate one or more tangible components in the facility. For example, the facility may include a valve component 281 that is assembled between a first component and a second component that transports gaseous materials throughout the facility. The controller 280 may actuate the valve component 281 from an open position to a closed position, and vice versa. For example, the components may be transporting gaseous materials across a distance in the facility, and when a leak source is detected originating from the second component that transports gaseous materials throughout the facility, the controller may issue a command to actuate the valve component 281 into a closed position, thus shutting off the flow of gas to the component with the source of the leak. In another example, the controller 280 may be communicatively coupled with a regulator 282 component.

Referring to FIG. 2, in one example, a user computing device 285 may comprise a processor, a memory, and/or a communication interface. The processor may process and analyze the data stored in the memory. In some embodiments, the memory may store computer-executable instructions that, when executed by the processor, cause a user computing device 285 to perform one or more of the steps disclosed herein. In some embodiments, the system 255 may determine total detected emissions and generate emissions reports based on signals received through the communications interface. As explained herein, in one example, the user computing device 285 may receive data from the emissions monitoring platform 260 and display a graphical user interface (GUI) on the user computing device 285 to enable a user to view emissions reports.

In some embodiments, the system 255 may generate alerts based on values received through the communications interface. The values may indicate that a dangerous gas leak has been detected in the facility due to anomalous sensor readings. The detection event may cause adjustment of one or more operating parameters of the facility. As a result of adjustment of the operating parameters, the facility may cause adjustments or halting/starting of one or more operations. In an alternative embodiment, the commands may be directly communicated, either wirelessly or in a wired fashion, to physical components at the facility such that the physical components include an interface to receive the commands and execute them.

Although FIG. 2 is not so limited, in some embodiments the user computing device 285 may include a desktop computer, a smartphone, a wireless device, a tablet computer, a laptop computer, and/or the like. The user computing device 285 may be physically located locally or remotely and may be connected by one or more communications links to one or more other devices in the system 255.

Although the elements of FIG. 2 are illustrated as logical block diagrams, the disclosure is not so limited. In particular, one or more of the representative boxes in FIG. 2 may be combined into a single box or the functionality performed by a single box may be divided across multiple existing or new representative boxes. Moreover, some boxes that are visually presented as being inside of another box may be moved such that they are partially or completely residing outside of that box. For example, FIG. 2 contemplates that data store 290 may be stored inside a firewall (e.g., internal to LAN 270) or stored on a publicly accessible network 275 to facilitate sharing between multiple facilities, in some examples.

Furthermore, the data stores 290 from multiple plant locations may be shared and holistically analyzed to identify one or more trends and/or patterns in the operation and behavior of the facility and/or components. In such a crowd-sourcing-type example, a distributed database arrangement may be provided where a database (e.g., data store) may simply serve as an interface through which multiple, separate data stores may be accessed. As such, a system 255 may access the database to analyze data collected by various sensors. In another example, the data values from a database from each facility may be combined and/or collated into a single database using which emissions monitoring platforms may perform various calculations.

While particular embodiments are illustrated in and described with respect to the drawings, it is envisioned that those skilled in the art may devise various modifications without departing from the spirit and scope of the appended claims. For example, the term "gas stream" incorporates examples involving a single gas, multiple gases, and a gas mixture, and the disclosure contemplates them being used interchangeably. Also, the term "emission indicator value" incorporates examples involving an emission value, and the disclosure contemplates them being used interchangeably in real world applications. Moreover, it will therefore be appreciated that the scope of the disclosure and the appended claims is not limited to the specific embodiments illustrated in and discussed with respect to the drawings and that modifications and other embodiments are intended to be included within the scope of the disclosure and appended drawings. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the disclosure and the appended claims.

We claim:

1. A computer system comprising:
   at least one processor;
   a data store configured to store archived data corresponding to plant operation of an industrial facility; and
   a non-transitory computer-readable memory storing computer-readable instructions that, when executed by the at least one processor, cause the at least one processor to:
   post-process the archived data, which corresponds to a combination of plant operation, algorithm, and graphical user interface, that allows evaluation of emission of the industrial facility, wherein the plant operation comprises a gas stream associated with gas plume detections in a first time interval;

receive, from the data store, the archived data associated with the first time interval;

determine, from the archived data, an overall response factor of a sensor, as equal to:

$$\frac{1}{X_1/F_1 + X_2/F_2 + X_3/F_3 + \ldots + X_n/F_n}$$

where $X_1$-$X_n$ are mole ratios of any gases in the gas stream, $F_1$-$F_n$ are individual response factors of species of the any gases in the gas stream;

determine an emission indicator value ($D_i$), based on detection events in the archived data, as follows:

$$D_i = \sum_{i=1}^{n} S_i F_i$$

where $S_i$ is an accumulative emission detection value for the first time interval from sensor i and $F_i$ is the overall response factor for the gas streams at the sensor i, wherein the determining excludes detection events corresponding to a maintenance activity;

determine, using the emission indicator value and corresponding overall response factor in the archived data for a second time interval, a first total emission indicator value for the industrial facility in the first time interval;

determine a difference in value between the first total emission indicator value for the industrial facility in the first time interval and a second total emission indicator value for the facility in a second time interval; and send an indication of the difference to cause a visual comparison on a fugitive emission evaluation dashboard on the graphical user interface showing emission levels in the industrial facility at different time intervals; and a user computing device configured to display, on the graphical user interface of a display device coupled to the user computing device, the indication of the difference between the first total emission indicator value for the industrial facility in the first time interval and the second total emission indicator value for the facility in the second time interval, wherein the graphical user interface is used to allow evaluation of improvement across operations lifecycle by combining fugitive emissions evaluation data with plant information (PI) data across operation, safety, and emission control of the industrial facility.

2. The computer system of claim 1, wherein the memory stores computer-readable instructions that, when executed by the at least one processor, cause the platform to determine, for the first time interval, the detection events based on the archived data associated with the first time interval and modeled baseline values corresponding to the first time interval.

3. The computer system of claim 2, wherein the memory stores computer-readable instructions that, when executed by the at least one processor, cause the platform to determine a detection event, among the detection events, at a first time (T1) based on a difference between the modeled baseline value at the first time and a value of a sensor detection peak at the first time based on the archived data associated with the first time interval exceeding a threshold.

4. The computer system of claim 1, wherein the computer-readable instructions, when executed by the at least one processor, cause the platform to:

receive, from the user computing device, indications of a maintenance time interval and a location associated with the maintenance activity;

determine, based on the location, the archived data associated with the maintenance time interval;

determine, based on the first time interval, one or more detection events in the archived data associated with the maintenance time interval at the location.

5. The computer system of claim 1, wherein the computer-readable instructions, when executed by the at least one processor, cause the platform to:

determine a third total emission indicator value in a third time interval and a fourth total emission indicator value in fourth time interval;

determine, based on a sum of the first total emission indicator value and the second total emission indicator value, a first aggregated total emission indicator value;

determine, based on a sum of the third total emission indicator value and the fourth total emission indicator value, a second aggregated total emission indicator value;

determine, based on a difference between the first aggregated emission indicator value and the second aggregated emission indicator value, an aggregated change in emissions; and send, to the user computing device, the first total emission indicator value, the second total emission indicator value, the third total emission indicator value, the fourth total emission indicator value, and the aggregated change in emissions.

6. The computer system of claim 5, wherein the user computing device is configured to:

display, on the display device, one or more of the first total emission indicator value, the second total emission indicator value, the third total emission indicator value, the fourth total emission indicator value, and the aggregated change in emissions.

7. The computer system of claim 5, wherein the determining the first total emission indicator value for the industrial facility comprises determining a sum of products of corresponding emission indicator values and corresponding response factors for the archived data.

8. The computer system of claim 7, wherein the user computing device is configured to:

display, on the display device, one or more of the total emission indicator value, the second total emission indicator value, the third total emission indicator value, the fourth total emission indicator value, and the aggregated change in emissions.

9. The computer system of claim 1, wherein the computer-readable instructions, when executed by the at least one processor, cause the platform to:

determine a third total emission indicator value for the facility in the first time interval;

determine a second difference between the first total emission indicator value and the third total emission indicator value; and send, to the user computing device, an indication of the second difference; and wherein the user computing device is configured to display, on the display device, one or more of the total emission indicator value, the third total emission indicator value, and the second difference.

10. The computer system of claim 9, wherein the determining the first total emission indicator value for the industrial facility comprises determining a sum of products of corresponding emission indicator values and corresponding response factors for the archived data.

\* \* \* \* \*